(12) United States Patent
Bar-Or

(10) Patent No.: US 8,227,457 B2
(45) Date of Patent: *Jul. 24, 2012

(54) METHOD FOR TREATMENT OF DISEASES

(75) Inventor: David Bar-Or, Englewood, CO (US)

(73) Assignee: DMI Acquisition Corp., Greenwood Village, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/276,810

(22) Filed: Oct. 19, 2011

(65) Prior Publication Data

US 2012/0035147 A1 Feb. 9, 2012

Related U.S. Application Data

(63) Continuation of application No. 12/820,398, filed on Jun. 22, 2010.

(60) Provisional application No. 61/219,185, filed on Jun. 22, 2009, provisional application No. 61/315,350, filed on Mar. 18, 2010.

(51) Int. Cl.
*A01N 43/00* (2006.01)
*A61K 31/33* (2006.01)
*A61K 31/58* (2006.01)

(52) U.S. Cl. ........................................ 514/183; 517/176

(58) Field of Classification Search .................. 514/183, 514/176
See application file for complete search history.

(56) References Cited

U.S. PATENT DOCUMENTS

| | | | |
|---|---|---|---|
| 3,135,743 A | 6/1964 | Clinton et al. | |
| 4,837,212 A | 6/1989 | Harrington et al. | |
| 4,975,537 A | 12/1990 | Aristoff et al. | |
| 4,994,443 A | 2/1991 | Folkman et al. | |
| 5,094,857 A | 3/1992 | Luderschmidt | |
| 5,372,996 A | 12/1994 | Labrie | |
| 5,407,926 A | 4/1995 | Clark | |
| 5,506,220 A | 4/1996 | Schwadrohn | |
| 5,620,921 A | 4/1997 | Sullivan | |
| 5,646,136 A | 7/1997 | Petrow et al. | |
| 5,679,666 A | 10/1997 | Clark | |
| 5,714,481 A | 2/1998 | Schwartz et al. | |
| 5,770,589 A | 6/1998 | Billson et al. | |
| 5,770,592 A | 6/1998 | Clark | |
| 5,929,111 A | 7/1999 | Conrow et al. | |
| 5,972,922 A | 10/1999 | Wilks et al. | |
| 5,990,099 A | 11/1999 | Clark | |
| 6,011,023 A | 1/2000 | Clark et al. | |
| 6,060,463 A | 5/2000 | Freeman | |
| 6,110,906 A | 8/2000 | Labrie | |
| 6,297,228 B1 | 10/2001 | Clark | |
| 6,333,317 B1 | 12/2001 | Lee et al. | |
| 6,413,540 B1 | 7/2002 | Yaacobi | |
| 6,610,674 B1 | 8/2003 | Schreiber | |
| 6,645,954 B2 | 11/2003 | Carruthers | |
| 6,663,865 B1 | 12/2003 | Borrelli et al. | |
| 6,936,599 B2 | 8/2005 | Voskuhl | |

| | | | |
|---|---|---|---|
| 2002/0055512 A1 | 5/2002 | Merin et al. | |
| 2003/0003144 A1 | 1/2003 | Keller | |
| 2003/0027772 A1 | 2/2003 | Breton | |
| 2003/0050291 A1 | 3/2003 | Arad | |
| 2003/0069232 A1 | 4/2003 | Chiou | |
| 2003/0232798 A1 | 12/2003 | Arad | |
| 2004/0063719 A1 | 4/2004 | Adams et al. | |
| 2004/0137068 A1 | 7/2004 | Bhushan | |
| 2004/0138187 A1 | 7/2004 | Reading et al. | |
| 2004/0204392 A1 | 10/2004 | Wood et al. | |
| 2004/0219208 A1 | 11/2004 | Kawamura et al. | |
| 2006/0233859 A1* | 10/2006 | Whitcup et al. | 424/427 |
| 2007/0010494 A1 | 1/2007 | Ehrhardt et al. | |
| 2007/0111972 A1 | 5/2007 | Bar-Or | |
| 2007/0173538 A1 | 7/2007 | Han et al. | |
| 2008/0193499 A1* | 8/2008 | Liu et al. | 424/423 |
| 2008/0214614 A1 | 9/2008 | Lampe et al. | |
| 2008/0249076 A1 | 10/2008 | Holm et al. | |
| 2008/0318875 A1 | 12/2008 | Chibber | |
| 2009/0105152 A1 | 4/2009 | Asami et al. | |
| 2010/0323991 A1 | 12/2010 | Bar-Or | |
| 2010/0324005 A1 | 12/2010 | Bar-Or | |
| 2011/0171306 A1 | 7/2011 | Bar-Or | |
| 2011/0171307 A1 | 7/2011 | Bar-Or | |

FOREIGN PATENT DOCUMENTS

| | | |
|---|---|---|
| EP | 0244178 | 11/1987 |
| EP | 0501056 | 9/1992 |
| EP | 061943 | 8/1994 |
| EP | 0939124 | 9/1999 |
| EP | 1236469 | 9/2002 |
| EP | 1236470 | 9/2002 |
| EP | 1236471 | 9/2002 |
| EP | 1003553 | 8/2004 |
| GB | 1123770 | 8/1968 |
| GB | 2263109 | 7/1993 |
| GB | 2345851 | 7/2000 |
| JP | 01-301623 | 12/1989 |
| JP | 02-042020 | 2/1990 |
| JP | 04-149132 | 5/1992 |
| JP | 2003081875 | 3/2003 |

(Continued)

OTHER PUBLICATIONS

"Danazol," http://www.drugs.com/pro/Danazol.html, copyright 2000-2010 (printed Dec. 10, 2010), 10 pages.

Adashi et al., "Direct biphasic effects of danazol on gonadotropin-dependent differentiation of cultured rat granulosa cells," Fertility and Sterility, Jun. 1986, vol. 45, No. 6, pp. 867-875.

Ahn et al., "Danazol for the treatment of idiopathic thrombocytopenic purpura," N Engl J Med, Jun. 1983, vol. 308(23), pp. 1396-1399 (Abstract Only).

(Continued)

*Primary Examiner* — Marcos Sznaidman
(74) *Attorney, Agent, or Firm* — Sheridan Ross P.C.

(57) ABSTRACT

The invention provides a method of inhibiting vascular hyperpermeability in an animal in need thereof. The method comprises administering a vascular-hyperpermeability-inhibiting amount of a danazol compound to the animal. The invention also provides a method of modulating the cytoskeleton of an endothelial cell in an animal. The method comprises administering an effective amount of a danazol compound to the animal.

9 Claims, 3 Drawing Sheets

FOREIGN PATENT DOCUMENTS

| | | |
|---|---|---|
| WO | WO 86/02554 | 5/1986 |
| WO | WO 91/19731 | 12/1991 |
| WO | WO 93/10141 | 5/1993 |
| WO | WO 95/18621 | 7/1995 |
| WO | WO 00/02564 | 1/2000 |
| WO | WO 01/04349 | 1/2001 |
| WO | WO 01/30337 | 5/2001 |
| WO | WO 01/53321 | 7/2001 |
| WO | WO 01/68053 | 9/2001 |
| WO | WO 02/11676 | 2/2002 |
| WO | WO 02/069977 | 9/2002 |
| WO | WO 2004/043480 | 5/2004 |
| WO | WO 2004/058289 | 7/2004 |
| WO | WO 2004/093852 | 11/2004 |
| WO | WO 2004/103406 | 12/2004 |
| WO | WO 2005/097121 | 10/2005 |
| WO | WO 2006/004795 | 1/2006 |
| WO | WO 2006/054119 | 5/2006 |
| WO | WO 2006/064291 | 6/2006 |
| WO | WO 2006/082588 | 8/2006 |
| WO | WO 2006/091459 | 8/2006 |
| WO | WO 2006/094027 | 9/2006 |
| WO | WO 2007/009087 | 1/2007 |
| WO | WO 2007/109363 | 9/2007 |
| WO | WO 2009/036108 | 3/2009 |

OTHER PUBLICATIONS

Ahn et al., "Danazol therapy for autoimmune hemolytic anemia," Ann Intern Med, Mar. 1985, vol. 102(3), pp. 298-301 (Abstract Only).

Ahn et al., "Long-term danazol therapy in autoimmune thrombocytopenia: unmaintained remission and age-dependent response in women," Ann Intern Med, Nov. 1989, vol. 111(9), pp. 723-729 (Abstract Only).

Ahn et al., "Low-dose danazol therapy in idiopathic thrombocytopenic purpura," Annals of Internal Medicine, 1987, vol. 107, pp. 177-181.

Ahn, "Efficacy of danazol in hematologic disorders," Acta Haematol, 1990, vol. 84(3), pp. 122-129 (Abstract Only).

Akoum et al., "Secretion of interleukin-6 by human endometriotic cells and regulation by proinflammatory cytokines and sex steroids," Hum Reprod, Oct. 1996, vol. 11(1), pp. 2269-2275 (Abstract Only).

Al-Abdullah et al., "C1-inhibitor—biochemical properties and clinical applications," Crit Rev Immunol, 1985, vol. 5(4), pp. 317-330.

Aleksandrovskii, "Antithrombin III, C1 inhibitor, methylglyoxal, and polymorphonuclear leukocytes in the development of vascular complications in diabetes mellitus," Thromb Res, Jul. 1992, vol. 67(2), pp. 179-189 (Abstract Only).

Alessandrino et al., "Evidence- and consensus-based practice guidelines for the therapy of primary myelodysplastic syndromes. A statement from the Italian Society of Hematology," Haematologica, Dec. 2002, vol. 87, No. 12, pp. 1286-1306 (Abstract Only).

Alexopoulou, "Erectile dysfunction and lower androgenicity in type 1 diabetic patients," Diabetes Metab (Paris), 2001, vol. 27, 329-336.

Al-Momen et al., "Low-dose danazol for vascular access and dialyzer thrombosis in hemodialysis patients," Haemostasis, 1992, vol. 22(1), pp. 12-16 (Abstract Only).

Ambriz-Fernandez et al., "Danazol in refractory autoimmune thrombocytopenic purpura (ATP). A new therapeutic sequence," Arch Invest Med (Mex), Jul.-Sep. 1985, vol. 16(3), pp. 294-304.

Author Unknown, "Clinical Trial of Tamoxifen: University of Wisconsin, Madison," internet article, http://www.alsa.org/patient/drug.cfm?id=671, date unknown, printed Dec. 3, 2007.

Avina-Zubieta et al. "Long-term effectivemess of danazol corticosteroids and cytotoxic drugs in the treatment of hematologic manifestations of systemic lupus erythematosus," Lupus, 2003, vol. 12(1), pp. 52-57 (Abstract only).

Avvakumov et al., "Subcellular distribution and selectivity of the protein-binding component of the recognition system for sex-hormone-binding protein-estradiol complex in human decidual endometrium," Biochimica et Biophysica Acta, 1986, vol. 881, pp. 489-498.

Balash et al., "Acute pancreatitis associated with danazol treatment for endometriosis," Hum Reprod, Jun. 1994, vol. 9(6), pp. 1163-1165 (Abstract Only).

Banavali et al., "Danazol in treatment of angio-immunoblastic lymphadenopathy," Cancer, Aug. 1989, vol. 64(3), pp. 613-615 (Abstract Only).

Banks et al., "Release of the angiogenic cytokine vascular endothelial growth factor (VEGF) from platelets: significance for VEGF measuremnts and cancer biology," British Journal of Cancer, 1998, vol. 77(6), pp. 956-964.

Barbieri et al., "Comparison of the pharmacology of nafarelin and danazol," Am J Obstet Gynecol, Feb. 1990, vol. 162, pp. 581-585.

Barbieri et al., "Danazol: endocrine pharmacology and therapeutic applications," American Journal of Obstetrics and Gynecology, Oct. 15, 1981, vol. 141(4), pp. 453-463 (Abstract Only).

Barcz et al., "Serum VEGF (vascular endothelial growth factor) concentration in patients with endometriosis," Ginekol Pol, Sep. 2000, vol. 71(9), pp. 993-1000 (Abstract Only).

Bedrossian et al., "Diabetic retinopathy treated with testosterone," AMA Arch Ophthalmol, Sep. 1953, vol. 50, pp. 277-281.

Bell, "Danazol, Premenstrual Tension, and Uveitis," Arch Ophthalmol, 1989, vol. 107, pp. 796.

Birjmohun et al., "Effects of short-term and long-term danazol treatment on lipoproteins, coagulation, and progression of atherosclerosis: two clinical trials in healthy volunteers and patients with hereditary angioedema," Clinical Therapeutics, 2008, vol. 30(12), pp. 2314-2323.

Bishop et al., "The effect of danazol on tumour control and weight loss in patients on tamoxifen therapy for advanced breast cancer: a randomized double-blind placebo controlled trial," European Journal of Cancer, 1993, vol. 29A, No. 6, pp. 814-818 (Abstract Only).

Blanco et al., "Successful therapy with danazol in refractory autoimmune thrombocytopenia associated with rheumatic diseases," Br J Rheumatol, Oct. 1997, vol. 36(10), pp. 1095-1099 (Abstract Only).

Bork et al., "Benefits and risks of danazol in hereditary angioedema: a long-term survey of 118 patients," Allergy Asthma Immunol, 2008, vol. 100(2), pp. 152-161.

Boucher et al., "Effect of hormonal agents on monocyte chemotactic protein-I expression by endometrial epithelial cells of women with endometriosis," Fertil Steril, Nov. 2000, vol. 74(5), pp. 969-975 (Abstract Only).

Braun et al., "Effect of danazol in vitro and in vivo on monocyte-mediated enhancement of endometrial cell proliferation in women with endometriosis," Fertility and Sterility, Jul. 1994, vol. 62, No. 1, pp. 89-95 (Abstract Only).

Bretza et al., "Hypertension: a complication of danazol therapy," Arch Intern Med, Oct. 1980, vol. 140(10), pp. 1379-1380.

Buttram, "Use of danazol in conservative surgery," J Reprod Med, Jan. 1990, vol. 35(1 Suppl), pp. 82-84 (Abstract Only).

Buzaid et al., "Management of myelodysplastic syndromes," Am. J. Med., Jun. 1986, vol. 80(6), pp. 1149-1157 (Abstract Only).

Carlstrom et al., "Peripheral levels of dehydroepiandrosterone sulfate, dehydroepiandrosterone, androstenedione, and testosterone following different doses of danazol," Acta Obstet Gynecol Scand Suppl, 1984, vol. 123, pp. 125-129.

Catalano, "Prolonged response to cyclosporin-A in hypoplastic refractory anemia and correlation with in vitro studies," Haematologica, 2000, vol. 85, pp. 133-138.

Cervera et al., "Danazol for systemic lupus erythematosus with refractory autoimmune thrombocytopenia or Evans' syndrome," J Rheumatol, Oct. 1995, vol. 22(10), pp. 1867-1871 (Abstract Only).

Chan et al., "Danazol therapy in autoimmune hemolytic anemia associated with systemic lupus erythematosus," J Rheumatol, Feb. 1991, vol. 18(2), pp. 280-282 (Abstract Only).

Chaurasia et al., "Sex hormones and diabetic retinopathy," Ann Ophthalmol, 1993, vol. 25, pp. 227-230.

Chevalier et al., "Danazol induced pancreatitis and hepatitis," Clin Rheumatol, Jun. 1990, vol. 9(2), pp. 239-241 (Abstract Only).

Colacurci et al., "Immune system and endometriosis," Acta Europaea Fertilitatis, May/Jun. 1991, vol. 22, No. 3, pp. 161-162 (Abstract Only).

Cole et al., "Danazol treatment of advanced prostate cancer: clinical and hormonal effects," The Prostate, 1986, vol. 9(1), pp. 15-20 (Abstract Only).

Connolly et al., "The effect of danazol in the MRL/lpr mouse model of autoimmune disease," Agents Actions, Aug. 1988, vol. 25(1-2), pp. 164-170 (Abstract Only).

Coombes et al., "Danazol Treatment for Advanced Breast Cancer," Cancer Chemotherapy and Pharmacology, 1983, vol. 10, pp. 194-195.

Coombes et al., "Danazol treatment of advanced breast cancer," Cancer Treatment Reports, Oct./Nov. 1980, vol. 63(10-11), pp. 1073-1076 (Abstract Only).

Crook et al., "Lipoprotein Lp(a) levels are reduced by danazol, an anabolic steroid," Atherosclerosis, 1992, vol. 92(1), pp. 41-47.

Damaj et al., "Remission of transformed myelodysplastic syndrome with fibrosis after danazol therapy," Eur J Haematol, Apr. 2002, vol. 68(4), pp. 233-235 (Abstract Only).

De Boer et al., "The Detection of Danazol and Its Significance in Doping Analysis," Journal of Analytical Toxicology, Jan./Feb. 1992, vol. 16, pp. 14-18.

De Oca Porto et al., "Gas chromatography/mass spectrometry characterization of urinary metabolites of danazol after oral administration in human," J. Chromatogr. B. Analyst. Technol. Biomed. Life Sci., Jan. 2006, vol. 830(1), pp. 178-183 (Abstract Only).

Diehl et al., "Autoimmune disease and chronic lymphocytic leukemia: autoimmune hemolytic anemia, oure red cell aplasia, and autoimmune thrombocytopenia," Seminars in Oncology, Feb. 1998, vol. 25(1), pp. 80-97 (Abstract Only).

Ding et al., "Sex differences of endogenous sex hormones and risk of type 2 diabetes: a systematic review and meta-analysis," JAMA, Mar. 15, 2006, vol. 295(11), pp. 1288-1299.

Dmowski, "Danazol. A synthetic steroid with diverse biologic effects," J Reprod Med, Jan. 1990, vol. 35 (1 Suppl), pp. 69-75.

Donaldson, "Danazol," The American Journal of Medicine, Sep. 1989, vol. 87, No. 3N, pp. 49N-55N (Abstract Only).

Drew et al., "Sex steroid regulation of microglial cell activation: relevance to multiple sclerosis," Ann NY Acad Sci, Dec. 2003, vol. 1007, pp. 329-334 (Abstract Only).

Du et al., "Administration of dehydroepiandrosterone suppresses experimental allergic encephalomyelitis in SJL/J mice," J Immunol, Dec. 2001, vol. 167(12); (Abstract Only).

El-Etr et al., "Steroid hormones in multiple sclerosis," J Neurol Sci, Jun. 2005, vol. 233(1-2), pp. 49-54 (Abstract Only).

El-Roeiy et al., "Danazol but not gonadotropin-releasing hormone agonists suppresses autoantibodies in endometriosis," Fertil Steril, Dec. 1988, vol. 50(6), pp. 864-871 (Abstract Only).

Fabiani et al., "Hereditary angioedema. Long-term follow-up of 88 patients. Experience of the Argentine Allergy and Immunology Institute," Allergol Immunopathol (Madr), Sep.-Oct. 2000, vol. 28(5), pp. 267-271 (Abstract Only).

Fabrykant et al., "Further Experience With Anabolic Steroids in Diabetic Retinopathy: Factors Precipitating Retinal Hemorrhages," Am J Med Sci, Sep. 1964, vol. 248, pp. 304-316.

Felinksi et al., "Glucocorticoid Regulation of Endothelial Cell Tight Junction Gene Expression: Novel Treatments for Diabetic Retinopathy," Current Eye Research, 2005, vol. 30, pp. 949-957.

Fenaux et al., "The role of danazol in the treatment of refractory idiopathic thrombocytopenic purpura. A report of 22 cases," Nouv Rev Fr Hematol, 1990, vol. 32(2), pp. 143-146 (Abstract Only).

Flores et al., "Danazol therapy in chronic immune thrombocytopenic purpura," Eur J. Haematol, Aug. 1990, vol. 45(2), pp. 109-110.

Flynn, "Expression of la and the production of interleukin 1 by peritone exudates macrophages activated in vivo by steroids," Life Sciences, Jun. 30, 1986, vol. 38, No. 26, pp. 2455-2460 (Abstract Only).

Forbes et al., "Dosage-related effects of danazol on sex hormone binding globulin and free and total androgen levels," Clinical Endocrinology, 1986, vol. 25, pp. 597-605.

Ford et al., "Changes in haematological indices, blood viscosity and inhibitors of coagulation during treatment of endometriosis with danazol," Thromb Haemost, Aug. 1994, vol. 72(2), pp. 218-221 (Abstract Only).

Fraser et al., "Danazol treatment and platelet function," Med J Aust, Apr. 1980, vol. 1(7), pp. 313-314 (Abstract Only).

Freedman et al., "Treatment of prostatic carcinoma by gonadotropin inhibition with danazol: a preliminary report," Scandinavian journal of urology and nephrology. Supplementum, 1980, vol. 55, pp. 173-175 (Abstract Only).

Fujimoto et al., "Progestins and danazol effect on cell-to-cell adhesion, and E-cadherin and alpha- and beta-catenin mRNA expressions," J Steroid Biochem Mol Biol, Mar. 1996, vol. 57(5-6), pp. 275-282.

Fukui et al., "Association between serum testosterone concentration and collagen degradation fragments in men with type 2 diabetes mellitus," Metabolism Clinical and Experimental, 2007, vol. 56, pp. 1228-1232.

Fukui et al., "Low serum testosterone concentration in middle-aged men with type 2 diabetes," Endocrine Journal, 2007, vol. 54(6), pp. 871-877.

Gagne et al., "Levels of vascular endothelial growth factor (VEGF) in serum of patients with endometriosis," Human Reproduction, 2003, vol. 18(8), pp. 1674-1680.

Gao et al., "Extracellular carbonic anhydrase mediates hemorrhagic retinal and cerebral vascular permeability through prekallikrein activation," Nat Med, Feb. 2007, vol. 13(2), pp. 181-188 [Epub Jan. 28, 2007] (Abstract Only).

Geffray et al., "Efficacy of danazol in autoimmune hemolytic anemia with cold agglutinins. 4 cases," Presse Med, Sep. 1992, vol. 21(31), pp. 1472-1475 (Abstract Only).

Gelfand et al., "Treatment of hereditary angioedema with danazol. Reversal of clinical and biochemical abnormalities," The New England Journal of Medicine, Dec. 1976, vol. 295(26), pp. 1444-1448 (Abstract Only).

Grange et al., "Fatal acute pulmonary fibrosis in a patient treated by danazol from thrombocytopenia," Am J Hematol, Oct. 1996, vol. 53(2), p. 149.

Graves et al., "Inflammation in amyotrophic lateral sclerosis spinal cord and brain is mediated by activated macrophages, mast cells and T cells," Amyotrophic Lateral Sclerosis, Dec. 2004, vol. 5(4), pp. 213-219 (Abstract Only).

Gurling, "Evaluation of an androgen, methylandrostenediol, in the treatment of diabetic retinopathy," Br J Ophthal, 1955, vol. 39, pp. 151-154.

Haffner et al., "Increased testosterone in type I diabetic subjects with severe retinopathy," Ophthalmology, Oct. 1990, vol. 97(10), pp. 1270-1274 (Abstract Only).

Hamed et al., "Pseudotumor cerebri induced by danazol," Am J Ophthalmol, Feb. 1989, vol. 107(2), pp. 105-110 (Abstract Only).

Han et al., "Approaches toward reversal of increased vascular permeability in C1 inhibitor deficient mice," Immunol Lett, Oct. 2003, vol. 89(2-3), pp. 155-160 (Abstract Only).

Haning et al., "Danazol and its principal metabolites interfere with binding of testosterone, cortisol, and thyroxin by plasma proteins," Clinical Chemistry, 1982, vol. 28, pp. 696-698 (Abstract Only).

Hardy et al., "Combination of Tamoxifen, Aminoglutethimide, Danazol and Medroxyprogesterone Acetate in Advanced Breast Cancer," European Journal of Cancer, 1990, vol. 26(7), pp. 824-827.

Harrison et al., "Maintenance therapy of cyclical mastalgia using low-dose danazol," J. R. Coll. Surg. Edinb., Apr. 1989, vol. 34, pp. 79-81.

Higa et al., "Autoimmune acquired form of angioedema that responded to danazol therapy," Intern Med, May 2002, vol. 41(5), pp. 398-402 (Abstract Only).

Higham et al., "A comparative study of danazol, a regimen of decreasing doses of danazol, and norethindrone in the treatment of objectively proven unexplained menorrhagia," American Journal of Obstetrics and Gynecology, Nov. 1993, vol. 169(5), pp. 1134-1139.

Hill et al., "Immunosuppressive effects of danazol in vitro," Fertility and Sterility, Sep. 1987, vol. 48, No. 3, pp. 414-418 (Abstract Only).

Holloway et al., "Prednisolone and danazol for treatment of immune-mediated anemia, thrombocytopenia, and ineffective erythroid regeneration in a dog," J Am Vet Med Assoc, Oct. 1990, vol. 197(8), pp. 1045-1048 (Abstract Only).

Hoots et al., "Aggressive combination therapy in the successful management of life-threatening intracranial hemorrhage in a patient with idiopathic thrombocytopenic purpura," Am J Pediatr Hematol Oncol, 1986, vol. 8(3), pp. 225-230 (Abstract Only).

Hopfl et al., "Long-term danazol therapy for hereditary angioedema," DMW (Deutsche Medizinische Wochenschrift), 1990, vol. 115(4), pp. 133-138 (includes English translation).

Horstman et al., "Danazol Distribution in Plasma and Cell Membranes as Related to Altered Cell Properties: Implications for Mechanism," American Journal of Hematology, 1995, vol. 50, pp. 179-187.

Houstmuller et al., "Treatment Of Diabetic Retinopathy With Anabolic Steroids," Netherl. Ophthal. Soc., 149th Meeting, Rotterdame 1962, Ophthamolgica, 1963, vol. 145, pp. 464-466.

Houstmuller et al., "Treatment of diabetic retinopathy with anabolic steroids," Ophthamologica, 1963, vol. 145, pp. 185-206.

Houstmuller, "The therapeutic applications of anabolic steroids in ophthalmology: biochemical results," Acta Endocrinol Suppl (Copenh), 1961, (Suppl 63), pp. 154-174.

Hsiao et al., "Low-dose danazol in the treatment of livedoid vasculitis," Dermatology, 1997, vol. 194(3), pp. 251-255 (Abstract only).

Hsieh et al., "Rhabdomyolysis and pancreatitis associated with coadministration of danazol 600 mg/d and lovastatin 40 mg/d," Clinical Therapeutics, 2008, vol. 30(7), pp. 1330-1335.

Hull et al., "Antiangiogenic Agents are Effective Inhibitors of Endometriosis," The Journal of Clinical Endocrinology & Metabolism, 2003, vol. 88(6), available at http://jcem.endojournals.org/cgi/content/full/88/6/2889, 20 pages.

Imai et al., "A gonadotropin-releasing hormone analogue impairs glucose tolerance in a diabetic patient," Eur J Obstet Gynecol Reprod Biol, 1998, vol. 76, pp. 121-122.

Jelkmann, "Pitfalls in the Measurement of Circulating Vascular Endothelial Growth Factor," Clinical Chemistry, 2001, vol. 47(4), pp. 617-623.

Jimenez et al., "Transendothelial migration of leukocytes is promoted by plasma from a subgroup of immune thrombocytopenic purpura patients with small-vessel ischemic brain disease," American Journal Of Hematology, Mar. 2008, vol. 83(3), pp. 206-211.

Jolicoeur et al., "Comparative effect of danazol and a GnRH agonist on monocyto chemotactic protein-1 expression by endometriotic cells," Am J Reprod Immunol, Feb. 2001, vol. 45(2), pp. 86-93 (Abstract Only).

Jones et al., "Response of patients with amyotrophic lateral sclerosis to testosterone therapy: endocrine evaluation," Archives of Neurology, Nov. 1982, vol. 39, No. 11, pp. 721-722 (Abstract Only).

Kasamatsu et al., "A case of lung cancer with hereditary angioedema treated effectively by chemo-radiotherapy with C1 esterase inhibitor concentrate and danazol," Nihon Kokyuki Gakkai Zasshi, May 2004, vol. 42(5), pp. 435-439 (Abstract Only).

Kirk et al., "Angiogenesis in multiple sclerosis: is it good, bad or an epiphenomenon?" J Neurol Sci, Feb. 2004, vol. 217(2), pp. 125-130 (Abstract Only).

Kochakian et al., "Anabolic-Andorgenic Steroids: A Historical Perspective and Definition," Anabolic Steroids in Sport and Exercise, 2000, Second Edition, Chapter 1, pp. 17-49.

Konerding, "Delivery of antiangiogenic and antioxidant drugs of opthalmic interest through a nanoporous inorganic filter," Expert Opinion Therapeutic Targets, 2004, vol. 8(3), pp. 255-258.

Kosano et al., "Steroid-induced cataract: other than in the whole animal system in the lens culture system, androgens, estrogens and progestins as well as glucocotticoids produce a loss of transparency of the lens," Dev Ophthalmol, 2002, vol. 35, pp. 161-168 (Abstract Only).

Koumantakis et al., "Soluble serum interleukin-2 receptor, interleukin-6 and interleukin-la in patients with endometriosis and in controls," Arch Gynecol Obstet, 1994, vol. 255(3), pp. 107-112 (Abstract Only).

Ledford et al., "Efficacy of Danazolin A Patient With Congenital Protein S Deficiency: Paradoxical Evidence for Decreased Platelet Activation With Increased Thrombin Generation," Thrombosis Research, Sep. 1997, vol. 87(5), pp. 473-482.

Liu et al., "Expression of vascular endothelial growth factor and endostatin in peritoneal fluid of patients with endometriosis," Di Yi Jun Yi Da Xue Xue Bao, Jan. 2004, vol. 24(1), pp. 69-71 (Abstract Only).

Lugassy et al., "Severe autoimmune hemolytic anemia with cold agglutinin and sclerodermic features—favorable response to danazol," Ann Hematol, Sep. 1993, vol. 67(3), pp. 143-144 (Abstract Only).

Maddox et al., "Low-dose danazol for mastalgia," The British Journal of Clinical Practice—Supplement, Nov. 1989, vol. 68, pp. 43-47.

Magri et al., "Comparative effect of the calcium antagonist verapamil and the synthetic steroids gestrinone and danazol on human monocyte phagocytosis in vitro," Gynecologic and Obstetric Investigation, 1997, vol. 43, No. 1, pp. 6-10 (Abstract Only).

Mahnke et al., "Vascular endothelial growth factor and interleukin-6 in peritoneal fluid of women with endometriosis," Fertil Steril, Jan. 2000, vol. 73(1), pp. 166-170 (Abstract Only).

Manoharan, "Danazol therapy in patients with immune cytopenias," Aust N Z J Med, Dec. 1987, vol. 17(6), pp. 613-614.

Margolis et al., "Anabolic steroid preparations in the complex therapy of diabetic retinopathy (Russian)," Vestn Oftalmol, 1960, pp. 64-66 (Database Embase Abstract Only).

Marini et al., "Therapeutic efficacy of danazol in myelodysplastic syndromes," Eur J Cancer Clin Oncol, Sep. 1988, vol. 24(9), pp. 1481-1490 (Abstract Only).

Marwaha et al., "Danazol therapy in immune thrombocytopenic purpura," Petiatr Hematol Oncol, 1990, vol. 7(2), pp. 193-198 (Abstract Only).

Matalliotakis et al., "Changes in immunologic variables (TNF-a,sCD8 and sCD4) during danazol treatment in patients with endometriosis," Int J Fertil Womens Med, May-Jun. 1997, vol. 42(3), pp. 211-214 (Abstract Only).

Matalliotakis et al., "Serum concentrations of growth factors in women with and without endometriosis: the action of anti-endometriosis medicines," Int Immunopharmacol, Jan. 2003, vol. 3(1), pp. 81-89.

Matalliotakis et al., "The possible anti-inflammatory role of circulating human leukocyt antigen levels in women with endometriosis after treatment with danazol and leuprorelin acetate depot," Mediators Inflamm, Apr. 2001, vol. 10(2), pp. 75-80 (Abstract Only).

Meeks et al., "Danazol increases the anticoagulant effect of warfarin," Ann Pharmacother, May 1992, vol. 26(5), pp. 641-642 (Abstract Only).

Menon et al., "Evidence that danazol inhibits gonadotropin-induced ovarian steroidogenesis at a point distal to gonadotropin-receptor interaction and adenosine 3',5' cyclic monophosphate formation," Am. J. Obstet. Gynecol, Feb. 15, 1980, vol. 136(4), pp. 524-530.

Miyamura et al., "[Severe aplastic anemia remarkably improved by a treatment with antilymphocyte globulin, high-dose methylprednisolone and danazol]," Rinsho Ketsueki, Jan. 1989, vol. 30(1), pp. 72-77 (Abstract Only).

Mori et al., "Danazol suppresses the production of interleukin-1 beta and tumor necrosis factor by human monocytes," American Journal of Reproductive Immunology, Oct. 1990, vol. 24, No. 2, pp. 45-50 (Abstract Only).

Mosier et al., "Amyotrophic lateral sclerosis immunoglobulins increase Ca2+ currents in a motoneuron cell line," Annals of Neurology (only abstract has been provided), Jan. 1995, vol. 37, No. 1, pp. 102-109 (Abstract Only).

Mylvaganam et al., "Immune modulation by danazol in autoimmune thrombocytopenia," Clinical Immunology and Immunopathology, Mar. 1987, vol. 42, No. 3, pp. 281-287 (Abstract Only).

Mylvaganam et al., "Very low dose danazolin idiopathic thrombocytopenic purpura and its role as an immune modulator," Am J Med Sci, Oct. 1989, vol. 298(4), pp. 215-220 (Abstract Only).

Noel et al., "Myelodysplastic syndromes. Pathogenesis, diagnosis and treatment," Crit Rev Oncol Hematol, 1992, vol. 12(3), pp. 193-215 (Abstract Only).

Offner et al., "A synthetic androstene derivative and a natural androstene metaolite inhibit relapsing-remitting EAE," J Neuroimmunol, Sep. 2002, vol. 130(1-2), pp. 128-139 (Abstract Only).

Ota et al., "Effect of danazol on the immunocompetent cells in the eutopic endometrium in patients with endometriosis: a multicenter cooperative study," Fertil Steril, Mar. 1996, vol. 65(3), pp. 545-551 (Abstract Only).

Ota et al., "Effects of danazol at the immunologic level in patients with adenomyosis, with special reference to autoantibodies: a multicenter cooperative study," Am J Obstet Gynecol, Aug. 1992, vol. 167(2), pp. 481-486 (Abstract Only).

Pakhale et al., "Rapidly progressive pulmonary fibrosis in a patient treated with danazol for idiopathic thrombocytopenic purpura," Can Respir J, Jan.-Feb. 2004, vol. 11(1), pp. 55-57 (Abstract Only).

Petz, "Treatment of autoimmune hemolytic anemias," Curr Opin Hematol, Nov. 2001, vol. 8(6), pp. 411-416 (Abstract Only).

Pignon et al., "Danazol in autoimmune haemolytic anaemia," Br J Haematol, Feb. 1993, vol. 83(2), pp. 343-345 (Abstract Only).

Pitts et al., "Remissions induced in hereditary angioneurotic edema with an attenuated androgen (danazol): correlation between concentrations of C1-inhibitor and the forth and second components of complement," J Lab Clin Med, Oct. 1978, vol. 92(4), pp. 501-507 (Abstract Only).

Port et al., "Effects of a 3beta-hydroxysteroid dehydrogenase inhibitor on monocyte-macrophage infiltration into rat corpus luteum and on apoptosis: relationship to the luteolytic action of prolactin," J Reprod Fertil, May 2000, vol. 119(1), pp. 93-99 (Abstract Only).

Powles et al., "Clinical Trial of Multiple Endocrine Therapy for Metastatic and Locally Advanced Breast Cancer with Tamoxifen-Aminoglutethimide-Danazol Compared to Tamoxifen Used Alone," Cancer Research (Suppl.), Aug. 1982, vol. 42, pp. 3458s-3460s.

Prada et al., "Regulation of C1 inhibitor synthesis," Immunobiology, Aug. 1998, vol. 199(2), pp. 377-388 (Abstract Only).

Pride et al., "Relief of asthma in two patients receiving danazol for endometriosis," Can Med Assoc J, Oct. 1984, vol. 131(7), pp. 763-764 (Abstract Only).

Pronzato et al., "A Phase II Study with Danazol in Metastatic Breast Cancer," American Journal of Clinical Oncology, 1987, vol. 10, No. 5, pp. 407-409.

Proudler et al., "Insulin propeptides in conditions associated with insulin resistance in humans and their relevance to insulin measurements," Metabolism, Apr. 1994, vol. 43(4), pp. 446-449.

Rigau et al., "[Danazol in autoimmune hemolytic anemias: an alternative treatment]," Med Clin (Barc), Mar. 1986, vol. 86(8), 349-350.

Roberts, "The History and Present Status of the Drug Development of Anabolic/Androgenic Steroids," available at http://www.mesomorphosis.com!articles/pharmacologylhistory-of-anabolic-steroids.htm, printed Dec. 29, 2009, publication date Jun. 1996, pp. 1-8.

Roselli et al., "The effect of anabolic-androgenic steroids on aromatase activity and androgen receptor binding in the rat preoptic area," Brain Res, May 1998, vol. 792(2), pp. 271-276 (Abstract Only).

Rosi et al., "Isolation, Synthesis, and Biological Activity of Five Metabolites of Danazol," Journal of Medicinal Chemistry, 1977, vol. 20(3), pp. 349-352.

Ruiz-Arguelles et al., "Protein S deficiency associated to anti-protein S antibodies in a patient with mixed connective-tissue disease and its reversal by danazol," Acta Haematol, 1993, vol. 89(4), pp. 206-208 (Abstract Only).

Ruiz-Irastorza et al., "Therapy of systemic lupus erythematosus: new agents and new evidence," Expert Opin Investig Drugs, Jul. 2000, vol. 9(7), pp. 1581-1593 (Abstract Only).

Sadek et al., "Prolonged complete remission of myelodysplastic syndrome treated with danazol, retinoic acid and low-dose prednisone," American Journal of Hematology, Aug. 2000, vol. 64(4), pp. 306-310 (Abstract Only).

Salek et al., "The influence of hormones and pharmaceutical agents on DHEA and DHEA-S concentrations: a review of clinical studies," J Clin Pharmacol, 2002, vol. 42, pp. 247-266.

Santaella et al., "Hereditary and acquired angioedema: experience with patients in Puerto Rico," P R Health Sci J, Mar. 2004, vol. 23(1), pp. 13-18 (Abstract Only).

Saskin et al., "Diabetic retinopathy. A new approach to therapy with a steroid hormone-testosterone propionate," Am J Ophthalmol, Apr. 1951, vol. 34(4), pp. 613-617.

Sato et al., "Comparative influence of steroid hormones and immunosuppressive agents on autoimmune expression in lacrim glands of a female mouse model of Sjogren's syndrome," Invest Ophthalmol Vis Sci, Apr. 1994, vol. 35(5), pp. 2632-2642 (Abstract Only).

Saulsbury et al., "Danazol therapy for chronic immune-mediated thrombocytopenic purpura in a patient with common variable immunodeficiency," Am j Pediatr Hematol Oncol, Fall 1991, vol. 13(3), pp. 326-329 (Abstract Only).

Schmaier et al., "Synthesis and expression of C1 inhibitor by human umbilical vein endothelial cells," The Journal of Biological Chemistry, Oct. 1989, vol. 264(30), pp. 18173-18179.

Schmidt et al., "Antioxidative and steroid systems in neurological and psychiatric disorders," The World Journal of Biological Psychiatry, 2005, vol. 6, pp. 26-35.

Schreiber et al., "Effect of danazol in immune thrombocytopenic purpura," N Engl J Med, Feb. 1987, vol. 316(9), pp. 503-508 (Abstract Only).

Schweppe et al., "[Effects of danazol therapy in endometriosis on the blood picture and blood coagulation]," Geburtshilfe Frauenheilkd, Sep. 1988, vol. 48(9), pp. 634-636 [Article in German] (Abstract Only).

Seifer et al., "Insulin-dependent diabetes mellitus associated with danazol," Am J Obstet Gynecol, Feb. 1990, vol. 162, pp. 474-475.

Seli et al., "Endometriosis: interaction of immune and endocrine systems," Semin Reprod Med, May 2003, vol. 21(2), pp. 135-144 (Abstract Only).

Selva et al., "[Danazol and autoimmune thrombocytopenia in systemic lupus erythematosus]," Med Clin (Barc), Apr. 1990, vol. 94(14), pp. 557-558 (1 page).

Shinmyozu et al., "[Occurrence of subdural hematoma closely associated with danazol administration in a patient with refractory ITP]," Rinsho Ketsueki, May 1990, vol. 31(5), pp. 674-675 [Article in Japanese] (Abstract Only).

Shinohara et al., "Idiopathic autoimmune hemolytic anemia successfully treated with danazol," Rinsho Ketsueki, Feb. 1990, vol. 31(2), pp. 256-257 (Abstract Only).

Singh et al., "Heterosteroids and drug research," Prog Med Chem, 1991, vol. 28, pp. 233-300.

Sullivan et al., "Androgen stimulation of lacrimal gland function in mouse mode of Sjogren's syndrome," J Steroid Biochem Mol Biol, Feb. 1997, vol. 60(3-4), pp. 237-245 (Abstract Only).

Sullivan et al., "Selectivity, specificity and kinetics of the androgen regulation of the ocular secretory immune system," Immunol Invest, May 1988, vol. 17(3), pp. 183-194 (Abstract Only).

Sur, "Experience with Danazol in the Treatment of Advanced Breast Cancer," Journal of the Indian Medical Association, Mar. 1989, vol. 87(3), pp. 71-72.

Szegedi et al., "Long-term danazol prophylaxis does not lead to increased carotid intima-media thickness in hereditary angioedema patients," Atherosclerosis, May 2008, vol. 198(1), pp. 184-191 [Epub Oct. 30, 2007] (Abstract Only).

Tainter et al., "Anabolic steroids in the management of the diabetic patient," New York State Journal of Medicine, Apr. 15, 1964, vol. 64, pp. 1001-1009.

Tan et al., "Danazol for treatment of refractory autoimmune hemolytic anaemia," Ann Acad med Singapore, Nov. 1989, vol. 18(6), pp. 707-709 (Abstract Only).

Thomas et al., "Effects of danazol on endothelial cell function and angiogenesis," Fertil Steril, Oct. 2007, vol. 88(4 Suppl), pp. 1065-1070 [Epub Mar. 23, 2007].

Tomino et al., "Clinical effect of danazol in patients with IgA nephropathy," Jpn J Med, May 1987, vol. 26(2), pp. 162-166.

Tomino et al., "Effect of danazol on solubilization of immune deposits in patients with IgA nephropathy," Am J Kidney Dis, Sep. 1984, vol. 4(2), pp. 135-140.

Tommassini et al., "Sex hormones modulate brain damage in multiple sclerosis: MRI evidence," J Neurol Neurosurg Psychiatry, Feb. 2005, vol. 76(2), pp. 272-275 (Abstract Only).

Tsang et al., "Effect of danazol on estradiol-17beta and progesterone secretion by porcine ovarian cells in vitro," Am. J. Obstet. Gynecol, Feb. 1979, vol. 133(3), pp. 256-259.

Valk, "Successes and Set-Backs in the Treatment of Diabetic Retinopathy With Anabolic Steroids During the Last Five Years," Netherl. Ophthal. Soc. 150th Meeting, Utrecht 1962, Ophthalmologica, 1963, vol. 146, pp. 325-350.

Van Vollenhoven et al., "Estrogen, progesterone, and testosterone: can they be used to treat autoimmune diseases?" Cleve Clin J Med, Jul.-Aug. 1994, vol. 61(4), pp. 276-284 (Abstract Only).

Vastag et al., "Endothelial cells cultured from human brain microvessels produce complement proteins factor H, factor B, C1 inhibitor, and C4," Immunobiology, Jul. 1998, vol. 199(1), pp. 5-13 (Abstract Only).

Vercellini et al., "Depot medroxyprogesterone acetate versus an oral contraceptive combined with very-low-dose danazol for long-term treatment of pelvic pain associated with endometriosis," Am J Obstet Gynecol, Aug. 1996, vol. 175(2), pp. 396-401.

Vercellini et al., "Very low dose danazol for relief of endometriosis-associated pelvic pain: a pilot study," Fertility and Sterility, Dec. 1994, vol. 62(6), pp. 1136-1142.

Vigano et al., "Danazol suppresses both spontaneous and activated human lymphocyte-mediated cytotoxicity," American Journal of Reproductive Immunology, Aug. 1992, vol. 28(1), pp. 38-42 (Abstract Only).

Vigano et al., "Immunosuppressive effect of danazol on lymphocyte-mediated cytotoxicity toward human endometrial stromal cells," Gynecological Endocrinology: The Official Journal of the International Society of Gynecological Endocrinology, Mar. 1994, vol. 8(1), pp. 13-19 (Abstract Only).

Watson et al., "Interactions between oestradiol and danazol on the growth of gastrointestinal tumour cells," Anticancer Research, Jan./Feb. 1993, vol. 13(1), pp. 97-102 (Abstract Only).

Webb et al., "Vascular endothelial growth factor (VEGF) is released from platelets during blood clotting: implications for measurement of circulating VEGF levels in clinical disease," Clin. Sci. (Lond), Apr. 1998, vol. 94(4), pp. 395-404 (Abstract Only).

Weiner, "Possible role of androgen receptors in amyotrophic lateral sclerosis: a hypothesis," Archives of Neurology, Mar. 1980, vol. 37(3), pp. 129-131 (Abstract Only).

Weinstock-Guttman et al., "What is new in the treatment of multiple sclerosis?" Drugs, Mar. 2000, vol. 59(3), pp. 401-410 (Abstract Only).

West et al., "Danazol for the treatment of refractory autoimmune thrombocytopenia in systemic lupus erythematosus," Ann Intern Med, May 1988, vol. 108(5), pp. 703-706 (Abstract Only).

Williams, "Metabolic effects of danazol," Am J Obstet Gynecol, Mar. 1991, vol. 164(3), pp. 933-934.

Wong, "Danazol in treatment of lupus thrombocytopenia," Asian Pac J Allergy Immunol, Dec. 1991, vol. 9(2), pp. 125-129 (Abstract Only).

International Search Report for International (PCT) Patent Application No. PCT/US10/39458, mailed Aug. 18, 2010.

Written Opinion for International (PCT) Patent Application No. PCT/US10/39458, mailed Aug. 18, 2010.

Extended European Search Report for European Patent Application No. 10792567.9, dated Oct. 17, 2011.

International Preliminary Report on Patentability for International (PCT) Patent Application No. PCT/US2010/039458, mailed Jan. 12, 2012.

Extended Search Report for European Patent Application No. 11009239.2, dated Feb. 3, 2012, 7 pages.

Wood "Microglia: A possible cellular target for pharmacological approaches to neurodegenerative disorders." Drug News and Perspectives, Apr. 1994, vol. 7, No. 3, pp. 138-157.

"Enrollment underway in Modrenal prostate cancer study," Thomson Reuters Drug News, Sep. 28, 2004, 1 page, XP007920464.

Dudas et al. "Protection against inflammatory neurodegeneration and glial cell death by 7 beta-hydroxy epiandrosterone, a novel neurosteroid," Neurobiol Dis, 2004, vol. 15, No. 2, pp. 262-268.

Matalliotakis et al. "The anti-inflammatory action of danazol and leuprorelin acetate depot on endometriosis is CRH independent," Inflammopharmacology, Jun. 2001, vol. 9, No. 3, pp. 249-255.

Surrey et al. "Direct effects of medroxyprogesterone acetate, danazol, and leuprolide acetate on endometrial stromal cell proliferation in vitro," Fertility and Serility, Aug. 1992, vol. 58, No. 2, pp. 273-278.

* cited by examiner

METHOD FOR TREATMENT OF DISEASES

CROSS REFERENCE TO RELATED APPLICATIONS

This present application is a continuation of U.S. patent application Ser. No. 12/820,398, filed Jun. 22, 2010, which claims the benefit of U.S. Provisional Patent Application Ser. No. 61/219,185, filed Jun. 22, 2009, and U.S. Provisional Patent Application Ser. No. 61/315,350, filed Mar. 18, 2010, the complete disclosures of which are incorporated herein by reference.

FIELD OF THE INVENTION

The invention relates to a method of inhibiting vascular hyperpermeability and the edema and other adverse effects that result from it. The invention also relates to a method of modulating the cytoskeleton of endothelial cells. Both methods comprise administering a danazol compound to an animal.

BACKGROUND

The vascular endothelium lines the inside of all blood vessels. It acts as the interface between the blood and the tissues and organs. The endothelium forms a semi-permeable barrier that maintains the integrity of the blood fluid compartment, but permits passage of water, ions, small molecules, macromolecules and cells in a regulated manner. Dysregulation of this process produces vascular leakage into underlying tissues. Leakage of fluid into tissues causing edema can have serious and life threatening consequences in a variety of diseases. Accordingly, it would be highly desirable to have a method for reducing edema, preferably at its earliest stage, and restoring the endothelial barrier to physiological.

SUMMARY OF THE INVENTION

The invention provides such a method. In particular, the invention provides a method of inhibiting vascular hyperpermeability and the edema and other adverse effects that result from it. The method comprises administering a vascular-hyperpermeability-inhibiting amount of a danazol compound to an animal in need thereof. Inhibition of vascular hyperpermeability according to the invention includes inhibition of paracellular-caused hyperpermeability and transcytosis-caused hyperpermeability. Recent evidence indicates that transcytosis-caused hyperpermeability is the first step of a process that ultimately leads to tissue and organ damage in many diseases and conditions. Accordingly, the present invention provides a means of early intervention in these diseases and conditions which can reduce, delay or even potentially prevent the tissue and organ damage seen in them.

The invention also provides a method of modulating the cytoskeleton of endothelial cells in an animal. The method comprises administering an effective amount of a danazol compound to the animal.

"Vascular hyperpermeability" is used herein to mean permeability of a vascular endothelium that is increased as compared to basal levels. "Vascular hyperpermeability," as used herein, includes paracellular-caused hyperpermeability and transcytosis-caused hyperpermeability.

"Paracellular-caused hyperpermeability" is used herein to mean vascular hyperpermeability caused by paracellular transport that is increased as compared to basal levels. Other features of "paracellular-caused hyperpermeability" are described below.

"Paracellular transport" is used herein to mean the movement of ions, molecules and fluids through the interendothelial junctions (IEJs) between the endothelial cells of an endothelium.

"Transcytosis-caused hyperpermeability" is used herein to mean vascular hyperpermeability caused by transcytosis that is increased as compared to basal levels.

"Transcytosis" is used herein to mean the active transport of macromolecules and accompanying fluid-phase plasma constituents across the endothelial cells of the endothelium. Other features of "transcytosis" are described below.

"Basal level" is used herein to refer to the level found in a normal tissue or organ.

"Inhibiting, "inhibit" and similar terms are used herein to mean to reduce, delay or prevent.

An animal is "in need of" treatment according to the invention if the animal presently has a disease or condition mediated by vascular hyperpermeability, exhibits early signs of such a disease or condition, or has a predisposition to develop such a disease or condition.

"Mediated" and similar terms are used here to mean caused by, causing, involving or exacerbated by, vascular hyperpermeability.

DETAILED DESCRIPTION OF THE PRESENTLY-PREFERRED EMBODIMENTS OF THE INVENTION

Figure 1:
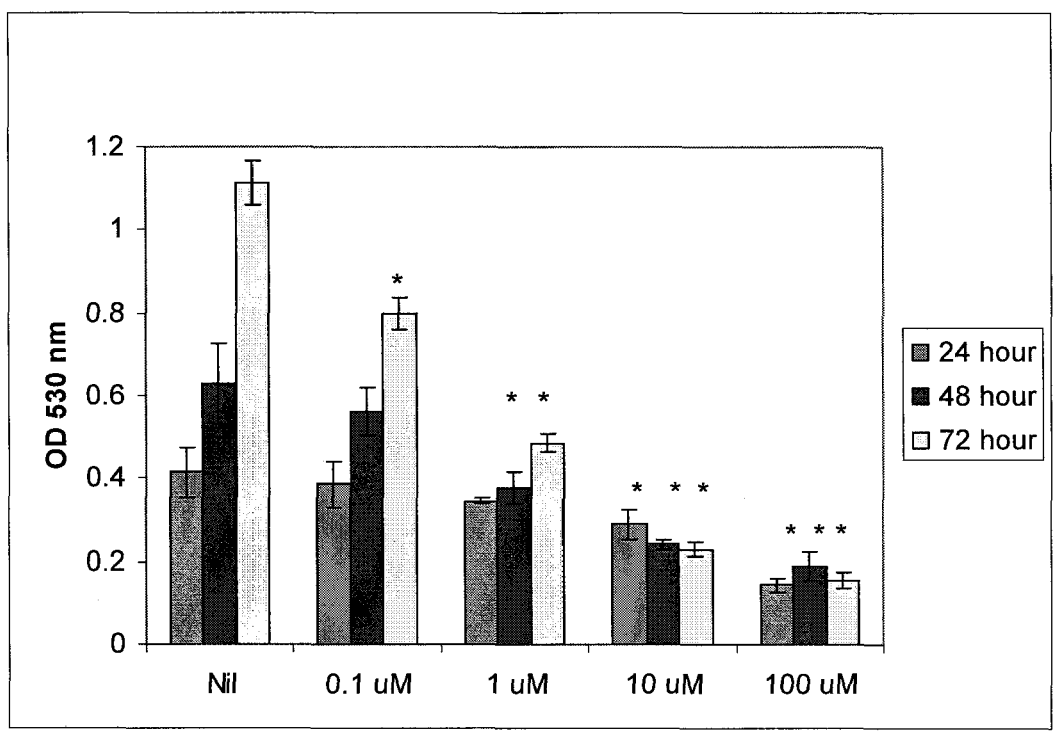
FIG. 1 shows the OD levels measured after incubation of HUVEC cells with danazol as a measure of its ability to prevent initial proliferation of endothelial cells.

The endothelium is a key gatekeeper controlling the exchange of molecules from the blood to the tissue parenchyma. It largely controls the permeability of a particular vascular bed to blood-borne molecules. The permeability and selectivity of the endothelial cell barrier is strongly dependent on the structure and type of endothelium lining the microvasculature in different vascular beds. Endothelial cells lining the microvascular beds of different organs exhibit structural differentiation that can be grouped into three primary morphologic categories: sinusoidal, fenestrated and continuous.

Sinusoidal endothelium (also referred to as "discontinuous endothelium") has large intercellular and intracellular gaps and no basement membrane, allowing for minimally restricted transport of molecules from the capillary lumen into the tissue and vice versa. Sinusoidal endothelium is found in liver, spleen and bone marrow.

Fenestrated endothelia are characterized by the presence of a large number of circular transcellular openings called fenestrae with a diameter of 60 to 80 nm. Fenestrated endothelia are found in tissues and organs that require rapid exchange of small molecules, including kidney (glomeruli, peritubular capillaries and ascending vasa recta), pancreas, adrenal glands, endocrine glands and intestine. The fenestrae are covered by thin diaphragms, except for those in mature, healthy glomeruli. See Ichimura et al., *J. Am. Soc. Nephrol.,* 19:1463-1471 (2008).

Continuous endothelia do not contain fenestrae or large gaps. Instead, continuous endothelia are characterized by an uninterrupted endothelial cell monolayer. Most endothelia in the body are continuous endothelia, and continuous endothelium is found in, or around, the brain (blood brain barrier), diaphragm, duodenal musculature, fat, heart, some areas of the kidneys (papillary microvasculature, descending vasa recta), large blood vessels, lungs, mesentery, nerves, retina (blood retinal barrier), skeletal muscle, testis and other tissues and organs of the body.

Endothelial transport in continuous endothelium can be thought of in a general sense as occurring by paracellular and transcellular pathways. The paracellular pathway is the pathway between endothelial cells, through the interendothelial junctions (IEJs). In unperturbed continuous endothelium, water, ions and small molecules are transported paracellularly by diffusion and convection. A significant amount of water (up to 40%) also crosses the endothelial cell barrier transcellularly through water-transporting membrane channels called aquaporins. A variety of stimuli can disrupt the organization of the IEJs, thereby opening gaps in the endothelial barrier. The formation of these intercellular gaps allows passage of fluid, ions, macromolecules (e.g., proteins) and other plasma constituents between the endothelial cells in an unrestricted manner. This paracellular-caused hyperpermeability produces edema and other adverse effects that can eventually result in damage to tissues and organs.

The transcellular pathway is responsible for the active transport of macromolecules, such as albumin and other plasma proteins, across the endothelial cells, a process referred to as "transcytosis." The transport of macromolecules occurs in vesicles called caveolae. Almost all continuous endothelia have abundant caveolae, except for continuous endothelia located in brain and testes which have few caveolae. Transcytosis is a multi-step process that involves successive caveolae budding and fission from the plasmalemma and translocation across the cell, followed by docking and fusion with the opposite plasmalemma, where the caveolae release their contents by exocytosis into the interstitium. Transcytosis is selective and tightly regulated under normal physiological conditions.

There is a growing realization of the fundamental importance of the transcellular pathway. Transcytosis of plasma proteins, especially albumin which represents 65% of plasma protein, is of particular interest because of its ability to regulate the transvascular oncotic pressure gradient. As can be appreciated, then, increased transcytosis of albumin and other plasma proteins above basal levels will increase the tissue protein concentration of them which, in turn, will cause water to move across the endothelial barrier, thereby producing edema.

Low density lipoproteins (LDL) are also transported across endothelial cells by transcytosis. In hyperlipidemia, a significant increase in transcytosis of LDL has been detected as the initial event in atherogenesis. The LDL accumulates in the subendothelial space, trapped within the expanded basal lamina and extracellular matrix. The subendothelial lipoprotein accumulation in hyperlipidema is followed by a cascade of events resulting in atheromatous plaque formation. Advanced atherosclerotic lesions are reported to be occasionally accompanied by the opening of IEJs and massive uncontrolled passage of LDL and albumin.

Vascular complications are a hallmark of diabetes. At the level of large vessels, the disease appears to be expressed as an acceleration of an atherosclerotic process. With respect to microangiopathy, alterations in the microvasculature of the retina, renal glomerulus and nerves cause the greatest number of clinical complications, but a continuously increasing number of investigations show that diabetes also affects the microvasculature of other organs, such as the mesentery, skin, skeletal muscle, heart, brain and lung, causing additional clinical complications. In all of these vascular beds, changes in vascular permeability appear to represent a hallmark of the diabetic endothelial dysfunction.

In continuous endothelium, capillary hyperpermeability to plasma macromolecules in the early phase of diabetes is explained by an intensification of transendothelial vesicular transport (i.e., by increased transcytosis) and not by the destabilization of the IEJs. In addition, the endothelial cells of diabetics, including those of the brain, have been reported to contain an increased number of caveolae as compared to normals, and glycated proteins, particularly glycated albumin, are taken up by endothelial cells and transcytosed at substantially greater rates than their native forms. Further, increased transcytosis of macromolecules is a process that continues beyond the early phase of diabetes and appears to be a cause of edema in diabetic tissues and organs throughout the disease if left untreated. This edema, in turn, leads to tissue and organ damage. Similar increases in transcellular transport of macromolecules have been reported in hypertension.

Paracellular-caused hyperpermeability is also a factor in diabetes and the vascular complications of diabetes. The IEJs of the paracellular pathway include the adherens junctions (AJs) and tight junctions (TJs). Diabetes alters the content, phosphorylation and localization of certain proteins in both the AJs and TJs, thereby contributing to increased endothelial barrier permeability.

In support of the foregoing discussion and for further information, see Frank et al., *Cell Tissue Res.,* 335:41-47 (2009), Simionescu et al., *Cell Tissue Res.,* 335:27-40 (2009); van den Berg et al., *J. Cyst. Fibros.,* 7(6): 515-519 (2008); Viazzi et al., *Hypertens. Res.,* 31:873-879 (2008); Antonetti et al., Chapter 14, pages 340-342, in *Diabetic Retinopathy* (edited by Elia J. Duh, Humana Press, 2008), Felinski et al., *Current Eye Research,* 30:949-957 (2005), Pascariu et al., *Journal of Histochemistry & Cytochemistry,* 52(1):65-76 (2004); Bouchard et al., *Diabetologia,* 45:1017-1025 (2002); Arshi et al., *Laboratory Investigation,* 80(8):1171-1184 (2000); Vinores et al., *Documenta Ophthalmologica,* 97:217-228 (1999); Oomen et al., *European Journal of Clinical Investigation,* 29:1035-1040 (1999); Vinores et al., *Pathol. Res. Pract.,* 194:497-505 (1998); Antonetti et al., *Diabetes,* 47:1953-1959 (1998), Popov et al., *Acta Diabetol.,* 34:285-293 (1997); Yamaji et al., *Circulation Research,* 72:947-957 (1993); Vinores et al., *Histochemical Journal,* 25:648-663 (1993); Beals et al., *Microvascular Research,* 45:11-19 (1993); Caldwell et al., *Investigative Ophthalmol. Visual Sci.,* 33(5):16101619 (1992).

Endothelial transport in fenestrated endothelium also occurs by transcytosis and the paracellular pathway. In addition, endothelial transport occurs by means of the fenestrae. Fenestrated endothelia show a remarkably high permeability to water and small hydrophilic solutes due to the presence of the fenestrae.

The fenestrae may or may not be covered by a diaphragm. The locations of endothelium with diaphragmed fenestrae include endocrine tissue (e.g., pancreatic islets and adrenal cortex), gastrointestinal mucosa and renal peritubular capillaries. The permeability to plasma proteins of fenestrated endothelium with diaphragmed fenestrae does not exceed that of continuous endothelium.

The locations of endothelium with nondiaphragmed fenestrae include the glomeruli of the kidneys. The glomerular fenestrated endothelium is covered by a glycocalyx that extends into the fenestrae (forming so-called "seive plugs") and by a more loosely associated endothelial cell surface layer of glycoproteins. Mathematical analyses of functional permselectivity studies have concluded that the glomerular endothelial cell glycocalyx, including that present in the fenestrae, and its associated surface layer account for the retention of up to 95% of plasma proteins within the circulation.

Loss of fenestrae in the glomerular endothelium has been found to be associated with proteinuria in several diseases, including diabetic nephropathy, transplant glomerulopathy, pre-eclampsia, diabetes, renal failure, cyclosporine nephropathy, serum sickness nephritis and Thy-1 nephritis. Actin rearrangement and, in particular, depolymerization of stress fibers have been found to be important for the formation and maintenance of fenestrae.

In support of the foregoing discussion of fenestrated endothelia and for additiona information, see Satchell et al., *Am. J. Physiol. Renal Physiol.*, 296:F947-F956 (2009); Haraldsson et al., *Curr. Opin. Nephrol. Hypertens.*, 18:331-335 (2009); Ichimura et al., *J. Am. Soc. Nephrol.*, 19:1463-1471 (2008); Ballermann, *Nephron Physiol.*, 106:19-25 (2007); Toyoda et al., *Diabetes*, 56:2155-2160 (2007); Stan, "Endothelial Structures Involved In Vascular Permeability," pages 679-688, *Endothelial Biomedicine* (ed. Aird, Cambridge University Press, Cambridge, 2007); Simionescu and Antohe, "Functional Ultrastructure of the Vascular Endothelium: Changes in Various Pathologies," pages 42-69, *The Vascular Endothelium I* (eds. Moncada and Higgs, Springer-Verlag, Berlin, 2006).

Endothelial transport in sinusoidal endothelium occurs by transcytosis and through the intercellular gaps (interendothelial slits) and intracellular gaps (fenestrae). Treatment of sinusoidal endothelium with actin filament-disrupting drugs can induce a substantial and rapid increase in the number of gaps, indicating regulation of the porosity of the endothelial lining by the actin cytoskeleton. Other cytoskeleton altering drugs have been reported to change the diameters of fenestrae. Therefore, the fenestrae-associated cytoskeleton probably controls the important function of endothelial filtration in sinusodial endotheluium. In liver, defenestration (loss of fenestrae), which causes a reduction in permeability of the endothelium, has been associated with the pathogenesis of several diseases and conditions, including aging, atherogenesis, atherosclerosis, cirrhosis, fibrosis, liver failure and primary and metastatic liver cancers. In support of the foregoing and for additional information, see Yokomori, *Med. Mol. Morphol.*, 41:1-4 (2008); Stan, "Endothelial Structures Involved In Vascular Permeability," pages 679-688, *Endothelial Biomedicine* (ed. Aird, Cambridge University Press, Cambridge, 2007); DeLeve, "The Hepatic Sinusoidal Endothelial Cell," pages 1226-1238, *Endothelial Biomedicine* (ed. Aird, Cambridge University Press, Cambridge, 2007); Pries and Kuebler, "Normal Endothelium," pages 1-40, *The Vascular Endothelium I* (eds. Moncada and Higgs, Springer-Verlag, Berlin, 2006); Simionescu and Antohe, "Functional Ultrastructure of the Vascular Endothelium: Changes in Various Pathologies," pages 42-69, *The Vascular Endothelium I* (eds. Moncada and Higgs, Springer-Verlag, Berlin, 2006); Braet and Wisse, *Comparative Hepatology*, 1:1-17 (2002); Kanai et al., *Anat. Rec.*, 244:175-181 (1996); Kempka et al., *Exp. Cell Res.*, 176:38-48 (1988); Kishimoto et al., *Am. J. Anat.*, 178:241-249 (1987).

The invention provides a method of inhibiting vascular hyperpermeability present in any tissue or organ containing or surrounded by continuous endothelium. As noted above, continuous endothelium is present in, or around, the brain (blood brain barrier), diaphragm, duodenal musculature, fat, heart, some areas of the kidneys (papillary microvasculature, descending vasa recta), large blood vessels, lungs, mesentery, nerves, retina (blood retinal barrier), skeletal muscle, skin, testis, umbilical vein and other tissues and organs of the body. Preferably, the continuous endothelium is that found in or around the brain, heart, lungs, nerves or retina.

The invention also provides a method of inhibiting vascular hyperpermeability present in any tissue or organ containing or surrounded by fenestrated endothelium. As noted above, fenestrated endothelium is present in, or around, the kidney (glomeruli, peritubular capillaries and ascending vasa recta), pancreas, adrenal glands, endocrine glands and intestine. Preferably, the fenestrated endothelium is that found in the kidneys, especially that found in the glomeruli of the kidneys.

Further, any disease or condition mediated by vascular hyperpermeability can be treated by the method of the invention. Such diseases and conditions include diabetes, hypertension and atherosclerosis.

In particular, the vascular complications of diabetes, including those of the brain, heart, kidneys, lung, mesentery, nerves, retina, skeletal muscle, skin and other tissues and organs containing continuous or fenestrated endothelium, can be treated by the present invention. These vascular complications include edema, accumulation of LDL in the subendothelial space, accelerated atherosclerosis, and the following: brain (accelerated aging of vessel walls), heart (myocardial edema, myocardial fibrosis, diastolic dysfunction, diabetic cardiomyopathy), kidneys (diabetic nephropathy), lung (retardation of lung development in the fetuses of diabetic mothers, alterations of several pulmonary physiological parameters and increased susceptibility to infections), mesentery (vascular hyperplasy), nerves (diabetic neuropathy), retina (macular edema and diabetic retinopathy) and skin (redness, discoloration, dryness and ulcerations).

Diabetic retinopathy is a leading cause of blindness that affects approximately 25% of the estimated 21 million Americans with diabetes. Although its incidence and progression can be reduced by intensive glycemic and blood pressure control, nearly all patients with type 1 diabetes mellitus and over 60% of those with type 2 diabetes mellitus eventually develop diabetic retinopathy. There are two stages of diabetic retinopathy. The first, non-proliferative retinopathy, is the earlier stage of the disease and is characterized by increased vascular permeability, microaneurysms, edema and eventually vessel closures. Neovascularization is not a component of the nonproliferative phase. Most visual loss during this stage is due to the fluid accumulating in the macula, the central area of the retina. This accumulation of fluid is called macular edema and can cause temporary or permanent decreased vision. The second stage of diabetic retinopathy is called proliferative retinopathy and is characterized by abnormal new vessel formation. Unfortunately, this abnormal neovascularization can be very damaging because it can cause bleeding in the eye, retinal scar tissue, diabetic retinal detachments or glaucoma, any of which can cause decreased vision or blindness. Macular edema can also occur in the proliferative phase.

Diabetic neuropathy is a common serious complication of diabetes. There are four main types of diabetic neuropathy:

peripheral neuropathy, autonomic neuropathy, radiculoplexus neuropathy and mononeuropathy. The signs and symptoms of peripheral neuropathy, the most common type of diabetic neuropathy, include numbness or reduced ability to feel pain or changes in temperature (especially in the feet and toes), a tingling or burning feeling, sharp pain, pain when walking, extreme sensitivity to the lightest touch, muscle weakness, difficulty walking, and serious foot problems (such as ulcers, infections, deformities and bone and joint pain). Autonomic neuropathy affects the autonomic nervous system that controls the heart, bladder, lungs, stomach, intestines, sex organs and eyes, and problems in any of these areas can occur. Radiculoplexus neuropathy (also called diabetic amyotrophy, femoral neuropathy or proximal neuropathy) usually affects nerves in the hips, shoulders or abdomen, usually on one side of the body. Mononeuropathy means damage to just one nerve, typically in an arm, leg or the face. Common complications of diabetic neuropathy include loss of limbs (e.g., toes, feet or legs), charcot joints, urinary tract infections, urinary incontinence, hypoglycemia unawareness (may even be fatal), low blood pressure, digestive problems (e.g., constipation, diarrhea, nausea and vomiting), sexual dysfunction (e.g., erectile dysfunction), and increased or decreased sweating. As can be seen, symptoms can range from mild to painful, disabling and even fatal.

Diabetic nephropathy is the most common cause of end-stage renal disease in the United States. It is a vascular complication of diabetes that affects the glomerular capillaries of the kidney and reduces the kidney's filtration ability. Nephropathy is first indicated by the appearance of hyperfiltration and then microalbuminuria. Heavy proteinuria and a progressive decline in renal function precede end-stage renal disease. Typically, before any signs of nephropathy appear, retinopathy has usually been diagnosed. Renal transplant is usually recommended to patients with end-stage renal disease due to diabetes. Survival rate at 5 years for patients receiving a transplant is about 60% compared with only 2% for those on dialysis.

Hypertension typically develops over many years, and it affects nearly everyone eventually. Uncontrolled hypertension increases the risk of serious health problems, including heart attack, congestive heart failure, stroke, peripheral artery disease, kidney failure, aneurysms, eye damage, and problems with memory or understanding.

Atherosclerosis also develops gradually. Atherosclerosis can affect the coronary arteries, the carotid artery, the peripheral arteries or the microvasculature, and complications of atherosclerosis include coronary artery disease (which can cause angina or a heart attack), coronary microvascular disease, carotid artery disease (which can cause a transient ischemic attack or stroke), peripheral artery disease (which can cause loss of sensitivity to heat and cold or even tissue death), and aneurysms.

Additional diseases and conditions that can be treated according to the invention include acute lung injury, acute respiratory distress syndrome (ARDS), age-related macular degeneration, cerebral edema, choroidal edema, choroiditis, coronary microvascular disease, cerebral microvascular disease, Eals disease, edema caused by injury (e.g., trauma or burns), edema associated with hypertension, glomerular vascular leakage, hemorrhagic shock, Irvine Gass Syndrome, ischemia, macular edema (e.g., caused by vascular occlusions, post-intraocular surgery (e.g., cataract surgery), uveitis or retinitis pigmentosa, in addition to that caused by diabetes), nephritis (e.g., glomerulonephritis, serum sickness nephritis and Thy-1 nephritis), nephropathies, nephrotic edema, nephrotic syndrome, neuropathies, organ failure due to tissue edema (e.g., in sepsis or due to trauma), pre-eclampsia, pulmonary edema, pulmonary hypertension, renal failure, retinal edema, retinal hemorrhage, retinal vein occlusions (e.g., branch or central vein occlusions), retinitis, retinopathies (e.g., artherosclerotic retinopathy, hypertensive retinopathy, radiation retinopathy, sickle cell retinopathy and retinopathy of prematurity, in addition to diabetic retinopathy), silent cerebral infarction, systemic inflammatory response syndromes (SIRS), transplant glomerulopathy, uveitis, vascular leakage syndrome, vitreous hemorrhage and Von Hipple Lindau disease. In addition, certain drugs, including those used to treat multiple sclerosis, are known to cause vascular hyperpermeability, and danazol can be used to reduce this unwanted side effect when using these drugs. Hereditary and acquired angioedema are expressly excluded from those diseases and conditions that can be treated according to the invention.

"Treat," "treating" or "treatment" is used herein to mean to reduce (wholly or partially) the symptoms, duration or severity of a disease or condition, including curing the disease, or to prevent the disease or condition.

Recent evidence indicates that transcytosis-caused hyperpermeability is the first step of a process that ultimately leads to tissue and organ damage in many diseases and conditions. Accordingly, the present invention provides a means of early intervention in these diseases and conditions which can reduce, delay or even potentially prevent the tissue and organ damage seen in them. For instance, an animal can be treated immediately upon diagnosis of one of the disease or conditions treatable according to the invention (those diseases and conditions described above). Alternatively, preferred is the treatment of animals who have early signs of, or a predisposition to develop, such a disease or condition prior to the existence of symptoms. Early signs of, and risk factors for, diabetes, hypertension and atherosclerosis are well known, and treatment of an animal exhibiting these early signs or risk factors can be started prior to the presence of symptoms of the disease or condition (i.e., prophylactically).

For instance, treatment of a patient who is diagnosed with diabetes can be started immediately upon diagnosis. In particular, diabetics should preferably be treated with a danazol compound prior to any symptoms of a vascular complication being present, although this is not usually possible, since most diabetics show such symptoms when they are diagnosed (see below). Alternatively, diabetics should be treated while nonproliferative diabetic retinopathy is mild (i.e., mild levels of microaneurysms and intraretinal hemorrhage). See *Diabetic Retinopathy*, page 9 (Ed. Elia Duh, M.D., Human Press, 2008). Such early treatment will provide the best chance of preventing macular edema and progression of the retinopathy to proliferative diabetic retinopathy. Also, the presence of diabetic retinopathy is considered a sign that other microvascular complications of diabetes exist or will develop (see Id., pages 474-477), and early treatment may also prevent or reduce these additional complications. Of course, more advanced diseases and conditions that are vascular complications of diabetes can also be treated with beneficial results.

However, as noted above, vascular complications are often already present by the time diabetes is diagnosed. Accordingly, it is preferable to prophylactically treat a patient who has early signs of, or a predisposition to develop, diabetes. These early signs and risk factors include fasting glucose that is high, but not high enough to be classified as diabetes ("prediabetes"), hyperinsulinemia, hypertension, dyslipidemia (high cholesterol, high triglycerides, high low-density lipoprotein, and/or low level of high-density lipoprotein), obesity (body mass index above 25), inactivity, over 45 years of age, inadequate sleep, family history of diabetes, minority race, history of gestational diabetes and history of polycystic ovary syndrome.

Similarly, treatment of a patient who is diagnosed with hypertension can be started immediately upon diagnosis. Hypertension typically does not cause any symptoms, but prophylactic treatment can be started in a patient who has a predispostion to develop hypertension. Risk factors for hypertension include age, race (hypertension is more common blacks), family history (hypertension runs in families), overweight or obesity, lack of activity, smoking tobacco, too much salt in the diet, too little potassium in the diet, too little vitamin D in the diet, drinking too much alcohol, high levels of stress, certain chronic conditions (e.g., high cholesterol, diabetes, kidney disease and sleep apnea) and use of certain drugs (e.g., oral contraceptives, amphetamines, diet pills, and some cold and allergy medications).

Treatment of a patient who is diagnosed with atherosclerosis can be started immediately upon diagnosis. However, it is preferable to prophylactically treat a patient who has early signs of, or a predispostion to develop, atherosclerosis. Early signs and risk factors for atherosclerosis include age, a family history of aneurysm or early heart disease, hypertension, high cholesterol, high triglycerides, insulin resistance, diabetes, obesity, smoking, lack of physical activity, unhealthy diet, and high level of C-reactive protein.

The method of the invention for inhibiting vascular hyperpermeability comprises administering an effective amount of a danazol compound to an animal in need thereof to inhibit the vascular hyperpermeability. As used here, "a danazol compound" means danazol, prodrugs of danazol and pharmaceutically acceptable salts of danazol and its prodrugs.

Danazol (17α-pregna-2,4-dien-20-yno[2,3-d]isoxazol-17β-ol) is a known synthetic steroid hormone. It's structure is:

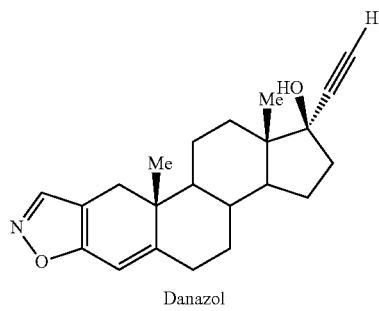

Danazol

Methods of making danazol are known in the art. See e.g., U.S. Pat. No. 3,135,743, and GB Patent No. 905,844. Also, danazol is available commercially from many sources, including Barr Pharmaceuticals, Inc., Lannett Co., Inc., sanofi-aventis Canada, Sigma-Aldrich, and Parchem Trading Ltd.

"Prodrug" means any compound which releases an active parent drug (danazol in this case) in vivo when such prodrug is administered to an animal. Prodrugs of danazol include danazol wherein the hydroxyl group is bonded to any group that may be cleaved in vivo to generate the free hydroxyl. Examples of danazol prodrugs include esters (e.g., acetate, formate, and benzoate derivatives) of danazol.

The pharmaceutically-acceptable salts of danazol and its prodrugs include conventional non-toxic salts, such as salts derived from inorganic acids (such as hydrochloric, hydrobromic, sulfuric, phosphoric, nitric, and the like), organic acids (such as acetic, propionic, succinic, glycolic, stearic, lactic, malic, tartaric, citric, glutamic, aspartic, benzoic, salicylic, oxalic, ascorbic acid, and the like) or bases (such as the hydroxide, carbonate or bicarbonate of a pharmaceutically-acceptable metal cation or organic cations derived from N,N-dibenzylethylenediamine, D-glucosamine, or ethylenediamine). The salts are prepared in a conventional manner, e.g., by neutralizing the free base form of the compound with an acid. In particular, isoxazoles, such as danazol, are weakly basic substances and will form acid-addition salts upon addition of strong acids and quaternary ammonium salts upon addition of esters of strong acids (e.g., an ester of a strong inorganic or organic sulfonic acid, preferably a lower-alkyl, lower alkenyl or lower aralkyl ester, such as methyl iodide, ethyl iodide, ethyl bromide, propyl bromide, butyl bromide, allyl bromide, methyl sulfate, methyl benezenesulfonate, methyl-p-toluene-sulfonate, benzyl chloride and the like). See U.S. Pat. No. 3,135,743.

As noted above, a danazol compound can be used to inhibit vascular hyperpermeability and to treat a disease or condition mediated by vascular hyperpermeability. To do so, the danazol compound is administered to an animal in need of treatment. Preferably, the animal is a mammal, such as a rabbit, goat, dog, cat, horse or human. Most preferably, the animal is a human.

Effective dosage forms, modes of administration and dosage amounts for the compounds of the invention (i.e., danazol, a prodrug of danazol or a pharmaceutically-acceptable salt of either one of them) may be determined empirically using the guidance provided herein. It is understood by those skilled in the art that the dosage amount will vary with the particular disease or condition to be treated, the severity of the disease or condition, the route(s) of administration, the duration of the treatment, the identity of any other drugs being administered to the animal, the age, size and species of the animal, and like factors known in the medical and veterinary arts. In general, a suitable daily dose of a compound of the present invention will be that amount of the compound which is the lowest dose effective to produce a therapeutic effect. However, the daily dosage will be determined by an attending physician or veterinarian within the scope of sound medical judgment. If desired, the effective daily dose may be administered as two, three, four, five, six or more sub-doses, administered separately at appropriate intervals throughout the day. Administration of the compound should be continued until an acceptable response is achieved.

Danazol compounds have previously been reported to inhibit angiogenesis. See PCT application WO 2007/009087. Surprisingly and quite unexpectedly, it has been found that danazol compounds can be used in the practice of the present invention at optimum doses that are about 100-1000 times lower than those previously reported for inhibiting angiogenesis and substantially less than those amounts currently administered to patients for the treatment of other diseases and conditions (typically 200-800 mg/day for an adult human). Uses of these lower doses of danazol compounds should avoid any significant side effects, perhaps all side effects, which will be especially advantageous for early or prophylatic treatment of diseases and conditions according to the present invention.

In particular, an effective dosage amount of a danazol compound for inhibiting vascular hyperpermeability will be from 0.1 ng/kg/day to 35 mg/kg/day, preferably from 40 ng/kg/day to 5.0 mg/kg/day, most preferably from 100 ng/kg/day to 1.5 mg/kg/day. An effective dosage amount will also be that amount that will result in a concentration in a relevant fluid (e.g., blood) from 0.0001 μM to 5 μM, preferably from 0.1 µM to 1.0 µM, more preferably from 0.1 µM to 0.5 µM, most preferably about 0.1 µM. An effective dosage amount will also be that amount that will result in a concentration in the tissue or organ to be treated of about 0.17% (weight/weight) or less, preferably from 0.00034% to 0.17%, most preferably 0.0034% to 0.017%. When given topically or locally, the danazol compound will preferably be administered at a concentration from 0.0001 µM to 5 µM, preferably from 0.1 µM to 1.0 µM, more preferably from 0.1 µM to 0.5 µM, most preferably about 0.1 µM, or at a concentration of about 0.17% (weight/weight) or less, preferably from 0.00034% to 0.17%, most preferably 0.0034% to 0.017%. When given orally to an adult human, the dose will preferably be from about 1 ng/day to about 100 mg/day, more preferably the dose will be from about 1 mg/day to about 100 mg/day, most preferably the dose will be from about 10 mg/day to about 90 mg/day, preferably given in two equal doses per day. Further, danazol is expected to accumulate in cells and tissues, so that an initial (loading) dose (e.g. 100 mg per day) may be reduced after a period of time (e.g., 2-4 weeks) to a lower maintenance dose (e.g. 1 mg per day) which can be given indefinitely without significant side effects, perhaps without any side effects. As used herein, a "vascular-hyperpermeability-inhibiting amount" of a danazol compound is defined to mean those amounts set forth above in this paragraph.

The invention also provides a method of modulating the cytoskeleton of endothelial cells in an animal. This embodiment of the invention is based on the discoveries that danazol inhibits F-actin stress fiber formation, causes the formation of cortical actin rings, enhances and prolongs the formation of cortical actin rings by sphingosine-1 phosphate (S1P), inhibits RhoA, increases phosphorylation of VE-cadherin, appears to activate barrier-stabilizing GTPases and appears to stabilize microtubules. Modulation of the cytoskeleton can reduce vascular hyperpermeability and increase vascular hypopermeability (i.e., permeability below basal levels), thereby returning the endothelium to homeostasis. Accordingly, those diseases and conditions mediated by vascular hyperpermeability can be treated (see above) and those diseases and conditions mediated by vascular hypopermeability can also be treated. The latter type of diseases and conditions include aging liver, atherogenesis, atherosclerosis, cirrhosis, fibrosis of the liver, liver failure and primary and metastatic liver cancers.

The method of modulating the cytoskeleton of endothelial cells comprises administering an effective amount of a danazol compound to the animal. "Danazol compound" and "animal" have the same meanings as set forth above.

Effective dosage forms, modes of administration and dosage amounts for the compounds of the invention (i.e., danazol, a prodrug of danazol or a pharmaceutically-acceptable salt of either one of them) for modulating the cytoskeleton may be determined empirically using the guidance provided herein. It is understood by those skilled in the art that the dosage amount will vary with the particular disease or condition to be treated, the severity of the disease or condition, the route(s) of administration, the duration of the treatment, the identity of any other drugs being administered to the animal, the age, size and species of the animal, and like factors known in the medical and veterinary arts. In general, a suitable daily dose of a compound of the present invention will be that amount of the compound which is the lowest dose effective to produce a therapeutic effect. However, the daily dosage will be determined by an attending physician or veterinarian within the scope of sound medical judgment. If desired, the effective daily dose may be administered as two, three, four, five, six or more sub-doses, administered separately at appropriate intervals throughout the day. Administration of the compound should be continued until an acceptable response is achieved.

In particular, an effective dosage amount of a danazol compound for modulating the cytoskeleton of endothelial cells will be from 0.1 ng/kg/day to 35 mg/kg/day, preferably from 40 ng/kg/day to 5.0 mg/kg/day, most preferably from 100 ng/kg/day to 1.5 mg/kg/day. An effective dosage amount will also be that amount that will result in a concentration in a relevant fluid (e.g., blood) from 0.0001 µM to 5 µM, preferably from 0.1 µM to 1.0 µM, more preferably from 0.1 µM to 0.5 µM, most preferably about 0.1 µM. An effective dosage amount will also be that amount that will result in a concentration in the tissue or organ to be treated of about 0.17% (weight/weight) or less, preferably from 0.00034% to 0.17%, most preferably 0.0034% to 0.017%. When given topically or locally, the danazol compound will preferably be administered at a concentration from 0.0001 µM to 5 µM, preferably from 0.1 µM to 1.0 µM, more preferably from 0.1 µM to 0.5 µM, most preferably about 0.1 µM, or at a concentration of about 0.17% (weight/weight) or less, preferably from 0.00034% to 0.17%, most preferably 0.0034% to 0.017%. When given orally to an adult human, the dose will preferably be from about 1 ng/day to about 100 mg/day, more preferably the dose will be from about 1 mg/day to about 100 mg/day, most preferably the dose will be from about 10 mg/day to about 90 mg/day, preferably given in two equal doses per day. Further, danazol is expected to accumulate in cells and tissues, so that an initial (loading) dose (e.g. 100 mg per day) may be reduced after a period of time (e.g., 2-4 weeks) to a lower maintenance dose (e.g. 1 mg per day) which can be given indefinitely without significant side effects, perhaps without any side effects.

The compounds of the present invention (i.e., danazol, prodrugs thereof and pharmaceutically-acceptable salts of either of them) may be administered to an animal patient for therapy by any suitable route of administration, including orally, nasally, parenterally (e.g., intravenously, intraperitoneally, subcutaneously or intramuscularly), transdermally, intraocularly and topically (including buccally and sublingually). Generally preferred is oral administration for any disease or condition treatable according to the invention. The preferred routes of administration for treatment of diseases and conditions of the eye are orally, intraocularly and topically. Most preferred is orally. It is quite unexpected and surprising that diseases of the eye can be treated by oral administration of a danazol compound, since successful treatment of such diseases and conditions by oral administration of a drug has not been previously reported. The preferred routes of administration for treatment of diseases and conditions of the brain are orally and parenterally. Most preferred is orally.

While it is possible for a compound of the present invention to be administered alone, it is preferable to administer the compound as a pharmaceutical formulation (composition). The pharmaceutical compositions of the invention comprise a compound or compounds of the invention as an active ingredient in admixture with one or more pharmaceutically-acceptable carriers and, optionally, with one or more other compounds, drugs or other materials. Each carrier must be "acceptable" in the sense of being compatible with the other ingredients of the formulation and not injurious to the animal. Pharmaceutically-acceptable carriers are well known in the art. Regardless of the route of administration selected, the compounds of the present invention are formulated into pharmaceutically-acceptable dosage forms by conventional methods known to those of skill in the art. See, e.g., *Remington's Pharmaceutical Sciences*.

Formulations of the invention suitable for oral administration may be in the form of capsules, cachets, pills, tablets, powders, granules or as a solution or a suspension in an aqueous or non-aqueous liquid, or an oil-in-water or water-in-oil liquid emulsions, or as an elixir or syrup, or as pastilles (using an inert base, such as gelatin and glycerin, or sucrose and acacia), and the like, each containing a predetermined amount of a compound or compounds of the present invention as an active ingredient. A compound or compounds of the present invention may also be administered as bolus, electuary or paste.

In solid dosage forms of the invention for oral administration (capsules, tablets, pills, dragees, powders, granules and the like), the active ingredient (i.e., danazol, a prodrug of danazol, a pharmaceutically-acceptable salt of either one of them, or combinations of the foregoing) is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monosterate; (8) absorbents, such as kaolin and bentonite clay; (9) lubricants, such as talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may be employed as fillers in soft and hard-filled gelatin capsules using such excipients as lactose or milk sugars, as well as high molecular weight polyethylene glycols and the like.

A tablet may be made by compression or molding optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter. These compositions may also optionally contain opacifying agents and may be of a composition that they release the active ingredient only, or preferentially, in a certain portion of the gastrointestinal tract, optionally, in a delayed manner. Examples of embedding compositions which can be used include polymeric substances and waxes. The active ingredient can also be in microencapsulated form.

Liquid dosage forms for oral administration of the compounds of the invention include pharmaceutically-acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active ingredient, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

The invention also provides pharmaceutical products suitable for treatment of the eye. Such pharmaceutical products include pharmaceutical compositions, devices and implants (which may be compositions or devices).

Pharmaceutical formulations (compositions) for intraocular injection of a compound or compounds of the invention into the eyeball include solutions, emulsions, suspensions, particles, capsules, microspheres, liposomes, matrices, etc. See, e.g., U.S. Pat. No. 6,060,463, U.S. Patent Application Publication No. 2005/0101582, and PCT application WO 2004/043480, the complete disclosures of which are incorporated herein by reference. For instance, a pharmaceutical formulation for intraocular injection may comprise one or more compounds of the invention in combination with one or more pharmaceutically-acceptable sterile isotonic aqueous or non-aqueous solutions, suspensions or emulsions, which may contain antioxidants, buffers, suspending agents, thickening agents or viscosity-enhancing agents (such as a hyaluronic acid polymer). Examples of suitable aqueous and nonaqueous carriers include water, saline (preferably 0.9%), dextrose in water (preferably 5%), buffers, dimethylsulfoxide, alcohols and polyols (such as glycerol, propylene glycol, polyethylene glycol, and the like). These compositions may also contain adjuvants such as wetting agents and emulsifying agents and dispersing agents. In addition, prolonged absorption of the injectable pharmaceutical form may be brought about by the inclusion of agents which delay absorption such as polymers and gelatin. Injectable depot forms can be made by incorporating the drug into microcapsules or microspheres made of biodegradable polymers such as polylactide-polyglycolide. Examples of other biodegradable polymers include poly(orthoesters), poly(glycolic) acid, poly(lactic) acid, polycaprolactone and poly(anhydrides). Depot injectable formulations are also prepared by entrapping the drug in liposomes (composed of the usual ingredients, such as dipalmitoyl phosphatidylcholine) or microemulsions which are compatible with eye tissue. Depending on the ratio of drug to polymer or lipid, the nature of the particular polymer or lipid components, the type of liposome employed, and whether the microcapsules or microspheres are coated or uncoated, the rate of drug release from microcapsules, microspheres and liposomes can be controlled.

The compounds of the invention can also be administered surgically as an ocular implant. For instance, a reservoir container having a diffusible wall of polyvinyl alcohol or polyvinyl acetate and containing a compound or compounds of the invention can be implanted in or on the sclera. As another example, a compound or compounds of the invention can be incorporated into a polymeric matrix made of a polymer, such as polycaprolactone, poly(glycolic) acid, poly(lactic) acid, poly(anhydride), or a lipid, such as sebacic acid, and may be implanted on the sclera or in the eye. This is usually accomplished with the animal receiving a topical or local anaesthetic and using a small incision made behind the cornea. The matrix is then inserted through the incision and sutured to the sclera.

The compounds of the invention can also be administered topically to the eye, and a preferred embodiment of the invention is a topical pharmaceutical composition suitable for application to the eye. Topical pharmaceutical compositions suitable for application to the eye include solutions, suspensions, dispersions, drops, gels, hydrogels and ointments. See, e.g., U.S. Pat. No. 5,407,926 and PCT applications WO 2004/058289, WO 01/30337 and WO 01/68053, the complete disclosures of all of which are incorporated herein by reference.

Topical formulations suitable for application to the eye comprise one or more compounds of the invention in an aqueous or nonaqueous base. The topical formulations can also include absorption enhancers, permeation enhancers, thickening agents, viscosity enhancers, agents for adjusting and/or maintaining the pH, agents to adjust the osmotic pressure, preservatives, surfactants, buffers, salts (preferably sodium chloride), suspending agents, dispersing agents, solubilizing agents, stabilizers and/or tonicity agents. Topical formulations suitable for application to the eye will preferably comprise an absorption or permeation enhancer to promote absorption or permeation of the compound or compounds of the invention into the eye and/or a thickening agent or viscosity enhancer that is capable of increasing the residence time of a compound or compounds of the invention in the eye. See PCT applications WO 2004/058289, WO 01/30337 and WO 01/68053. Exemplary absorption/permeation enhancers include methysulfonylmethane, alone or in combination with dimethylsulfoxide, carboxylic acids and surfactants. Exemplary thickening agents and viscosity enhancers include dextrans, polyethylene glycols, polyvinylpyrrolidone, polysaccharide gels, Gelrite®, cellulosic polymers (such as hydroxypropyl methylcellulose), carboxyl-containing polymers (such as polymers or copolymers of acrylic acid), polyvinyl alcohol and hyaluronic acid or a salt thereof.

Liquid dosage forms (e.g., solutions, suspensions, dispersions and drops) suitable for treatment of the eye can be prepared, for example, by dissolving, dispersing, suspending, etc. a compound or compounds of the invention in a vehicle, such as, for example, water, saline, aqueous dextrose, glycerol, ethanol and the like, to form a solution, dispersion or suspension. If desired, the pharmaceutical formulation may also contain minor amounts of non-toxic auxillary substances, such as wetting or emulsifying agents, pH buffering agents and the like, for example sodium acetate, sorbitan monolaurate, triethanolamine sodium acetate, triethanolamine oleate, etc.

Aqueous solutions and suspensions suitable for treatment of the eye can include, in addition to a compound or compounds of the invention, preservatives, surfactants, buffers, salts (preferably sodium chloride), tonicity agents and water. If suspensions are used, the particle sizes should be less than 10 μm to minimize eye irritation. If solutions or suspensions are used, the amount delivered to the eye should not exceed 50 μl to avoid excessive spillage from the eye.

Colloidal suspensions suitable for treatment of the eye are generally formed from microparticles (i.e., microspheres, nanospheres, microcapsules or nanocapsules, where microspheres and nanospheres are generally monolithic particles of a polymer matrix in which the formulation is trapped, adsorbed, or otherwise contained, while with microcapsules and nanocapsules the formulation is actually encapsulated). The upper limit for the size of these microparticles is about 5μ to about 10μ.

Ophthalmic ointments suitable for treatment of the eye include a compound or compounds of the invention in an appropriate base, such as mineral oil, liquid lanolin, white petrolatum, a combination of two or all three of the foregoing, or polyethylene-mineral oil gel. A preservative may optionally be included.

Ophthalmic gels suitable for treatment of the eye include a compound or compounds of the invention suspended in a hydrophilic base, such as Carpobol-940 or a combination of ethanol, water and propylene glycol (e.g., in a ratio of 40:40:20). A gelling agent, such as hydroxyethylcellulose, hydroxypropylcellulose, hydroxypropylmethylcellulose or ammoniated glycyrrhizinate, is used. A preservative and/or a tonicity agent may optionally be included.

Hydrogels suitable for treatment of the eye are formed by incorporation of a swellable, gel-forming polymer, such as those listed above as thickening agents or viscosity enhancers, except that a formulation referred to in the art as a "hydrogel" typically has a higher viscosity than a formulation referred to as a "thickened" solution or suspension. In contrast to such preformed hydrogels, a formulation may also be prepared so to form a hydrogel in situ following application to the eye. Such gels are liquid at room temperature but gel at higher temperatures (and thus are termed "thermoreversible" hydrogels), such as when placed in contact with body fluids. Biocompatible polymers that impart this property include acrylic acid polymers and copolymers, N-isopropylacrylamide derivatives and ABA block copolymers of ethylene oxide and propylene oxide (conventionally referred to as "poloxamers" and available under the Pluronic® tradename from BASF-Wayndotte).

Preferred dispersions are liposomal, in which case the formulation is enclosed within liposomes (microscopic vesicles composed of alternating aqueous compartments and lipid bilayers).

Eye drops can be formulated with an aqueous or nonaqueous base also comprising one or more dispersing agents, solubilizing agents or suspending agents. Drops can be delivered by means of a simple eye dropper-capped bottle or by means of a plastic bottle adapted to deliver liquid contents dropwise by means of a specially shaped closure.

The compounds of the invention can also be applied topically by means of drug-impregnated solid carrier that is inserted into the eye. Drug release is generally effected by dissolution or bioerosion of the polymer, osmosis, or combinations thereof. Several matrix-type delivery systems can be used. Such systems include hydrophilic soft contact lenses impregnated or soaked with the desired compound of the invention, as well as biodegradable or soluble devices that need not be removed after placement in the eye. These soluble ocular inserts can be composed of any degradable substance that can be tolerated by the eye and that is compatible with the compound of the invention that is to be administered. Such substances include, but are not limited to, poly(vinyl alcohol), polymers and copolymers of polyacrylamide, ethylacrylate and vinylpyrrolidone, as well as cross-linked polypeptides or polysaccharides, such as chitin.

Dosage forms for the other types of topical administration (i.e., not to the eye) or for transdermal administration of compounds of the invention include powders, sprays, ointments, pastes, creams, lotions, gels, solutions, patches, drops and inhalants. The active ingredient may be mixed under sterile conditions with a pharmaceutically-acceptable carrier, and with any buffers, or propellants which may be required. The ointments, pastes, creams and gels may contain, in addition to the active ingredient, excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays can contain, in addition to the active ingredient, excipients such as lactose, talc, silicic acid, aluminum hydroxide, calcium silicates and polyamide powder or mixtures of these substances. Sprays can additionally contain customary propellants such as chlorofluorohydrocarbons and volatile unsubstituted hydrocarbons, such as butane and propane. Transdermal patches have the added advantage of providing controlled delivery of compounds of the invention to the body. Such dosage forms can be made by dissolving, dispersing or otherwise incorporating one or more compounds of the invention in a proper medium, such as an elastomeric matrix material. Absorption enhancers can also be used to increase the flux of the compound across the skin. The rate of such flux can be controlled by either providing a rate-controlling membrane or dispersing the compound in a polymer matrix or gel. A drug-impregnated solid carrier (e.g., a dressing) can also be used for topical administration.

Pharmaceutical formulations include those suitable for administration by inhalation or insufflation or for nasal administration. For administration to the upper (nasal) or lower respiratory tract by inhalation, the compounds of the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide, or other suitable gas. In the case of a pressurized aerosol, the dosage unit may be determined by providing a valve to deliver a metered amount.

Alternatively, for administration by inhalation or insufflation, the composition may take the form of a dry powder, for example, a powder mix of one or more compounds of the invention and a suitable powder base, such as lactose or starch. The powder composition may be presented in unit dosage form in, for example, capsules or cartridges, or, e.g., gelatin or blister packs from which the powder may be administered with the aid of an inhalator, insufflator or a metered-dose inhaler.

For intranasal administration, compounds of the invention may be administered by means of nose drops or a liquid spray, such as by means of a plastic bottle atomizer or metered-dose inhaler. Liquid sprays are conveniently delivered from pressurized packs. Typical of atomizers are the Mistometer (Wintrop) and Medihaler (Riker).

Nose drops may be formulated with an aqueous or non-aqueous base also comprising one or more dispersing agents, solubilizing agents or suspending agents. Drops can be delivered by means of a simple eye dropper-capped bottle or by means of a plastic bottle adapted to deliver liquid contents dropwise by means of a specially shaped closure.

Pharmaceutical compositions of this invention suitable for parenteral administrations comprise one or more compounds of the invention in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, solutes which render the formulation isotonic with the blood of the intended recipient or suspending or thickening agents. Also, drug-coated stents may be used.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as wetting agents, emulsifying agents and dispersing agents. It may also be desirable to include isotonic agents, such as sugars, sodium chloride, and the like in the compositions. In addition, prolonged absorption of the injectable pharmaceutical form may be brought about by the inclusion of agents which delay absorption such as aluminum monosterate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug is accomplished by dissolving or suspending the drug in an oil vehicle.

Injectable depot forms are made by forming microencapsule matrices of the drug in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue. The injectable materials can be sterilized for example, by filtration through a bacterial-retaining filter.

The formulations may be presented in unit-dose or multi-dose sealed containers, for example, ampules and vials, and may be stored in a lyophilized condition requiring only the addition of the sterile liquid carrier, for example water for injection, immediately prior to use. Extemporaneous injection solutions and suspensions may be prepared from sterile powders, granules and tablets of the type described above.

A danazol compound may be given alone to treat a disease or condition involving vascular hyperpermeability or dysfunction of the cytoskeleton. Alternatively, the danazol compound may be given in combination with one or more other treatments or drugs suitable for treating the disease or condition. For instance, the danazol compound can be administered prior to, in conjunction with (including simultaneously with), or after the other treatment or drug. In the case of another drug, the drug and the danazol compound may be administered in separate pharmaceutical compositions or as part of the same pharmaceutical composition. Suitable drugs are described in U.S. application Ser. No. 12/820,325, the complete disclosure of which is incorporated herein by reference.

As used herein, "a" or "an" means one or more.

Additional objects, advantages and novel features of the present invention will become apparent to those skilled in the art by consideration of the following non-limiting examples.

EXAMPLES

Example 1

Danazol's Effects on Angiogenesis (Comparative)

A. HUVEC Cell Proliferation
Protocol:

Primary human umbilical vein endothelial cells (HUVECs) and EGM-2 growth medium were obtained from Cambrex (Walkersville, Md.). The cells were passaged in medium supplemented with 2% fetal calf serum (FCS) in tissue culture flasks at 37° C. and 5% $CO_2$. Subculturing was performed using trypsin when 60-80% confluence was obtained as specified by the supplier.

Cryopreserved ampoules of passage 2 HUVECs were thawed and plated in 96 well tissue culture plates at 5,000 cells/$cm^2$. A 50 mM stock solution of danazol was prepared in ethanol and the FCS in the medium was increased to 5% to keep danazol in solution. The cells were treated with medium containing final concentrations of danazol ranging from 0.1 to 100 µM in triplicates. 24, 48, and 72 hour incubations were performed and cell proliferation was determined utilizing Celltiter 96 $AQ_{ueous}$ One Solution Cell Proliferation assay from Promega (Madison, Wis.). In short, medium was aspirated from each well and the cells were washed with 200 µl Hepes buffered saline (HBSS) from Cambrex warmed to 37° C. 100 µl diluted celltiter solution (15 µl stock+85 µl EGM-2 containing 0.1% FCS) were added to each well and incubated for an additional 4 hours. Optical density was determined by microplate reader using a 530 nm filter after blank subtraction and data presented as OD±standard deviation. The final concentration of ethanol in the wells was less then 0.2% and had no effect on cell proliferation or viability.

All data are presented as representative experiments done in triplicate. Differences between subsets were analyzed using student t-test in Microsoft Excel. P<0.05 was considered statistically significant.

Results, Observations and Discussion:

Culturing primary HUVECs in the presence of danazol decreased the OD obtained from the Promega celltiter proliferation assay in a time and dose dependent fashion (FIG. 1). The celltiter assay is based on the reduction of the assay solution by dehydrogenase enzymes to a formazan dye that directly correlates to cell number.

Danazol treatment at 24 hours seemed to be effective only at very high doses. Significant decreases (p value <0.05) in assay OD were seen at 10 µM or greater concentrations of danazol. The OD detected in the nil wells was 0.414±0.06 and treatment with 10 µM danazol decreased the OD to 0.288±0.037 while 100 µM to 0.162±0.017, equating to percent inhibitions of 30% and 65% respectively.

At 48 hours, the inhibition observed was significant even at levels of 1 µM. The nil reading obtained after 48 hours in culture increased to 0.629±0.095 and was reduced to 0.378±0.037 by 1 µM, 0.241±0.012 by 10 µM, and 0.19±0.033 by 100 µM (or percent inhibitions of 40%, 61%, and 70% respectively).

After 72 hours, all danazol treatments tested exhibited significant reduction in HUVEC proliferation. The OD obtained in nil wells was 1.113±0.054 and after 0.1 µM treatment fell to 0.798±0.037, 1 µM to 0.484±0.022, 10 µM to 0.229±0.016, and 100 µM to 0.156±0.018 (inhibitions of 28%, 57%, 80%, and 86% respectively).

Examination of the OD obtained from all 100 µM danazol doses was consistent at all time points indicating a complete arrest of cell proliferation at this concentration.

In summary, danazol exhibited strong inhibition of endothelial cell proliferation.

B. HUVEC Tube Formation
Protocol:

To investigate the formation of capillary-like structures by HUVECs, the Angiogenesis System: Endothelial Cell Tube Formation Assay was purchased from BD Biosciences (San Jose, Calif.) and used according to the manufacturer's protocol. In brief, 100,000 HUVECs were seeded onto rehydrated matrigel plugs in 96 well tissue culture plates in the presence of 5% FCS to induce tube formation. Danazol was added to final concentrations of 1 µM, 10 µM, or 50 µM and LY294002 (positive control) was added at 50 µM. After 18 hours the wells were photographed using a Kodak DCS Pro SLR/N digital camera (Rochester, N.Y.) mounted on an inverted microscope. Ethanol treated wells were included to determine if the vehicle had any effects on cell differentiation.

Figure 2:
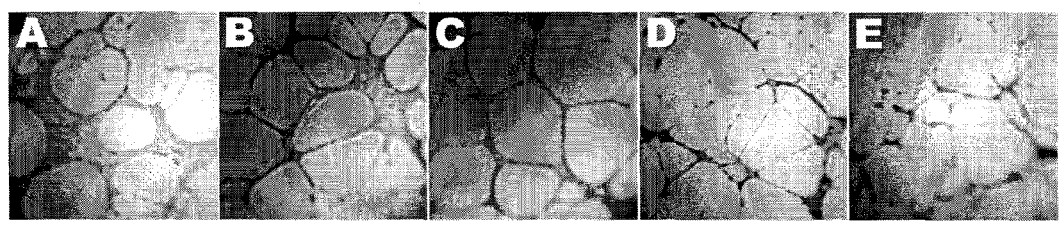
FIG. 2 shows photographs of HUVEC cells taken after incubation with danazol as a measure of its ability to prevent tube formation of endothelial cells. A=control; B=1 µM danazol, C=10 µM danazol, D=50 µM danazol and E=50 µM LY294002.

Results, Observations and Discussion:

To elucidate if danazol can prevent the formation of tube-like structures by HUVEC, 96 well plates containing matrigel plugs were used. Endothelial cells when cultured in the presence of angiogenic substances and supplied with an extracellular matrix scaffold will differentiate into structures loosely resembling capillary vessels. HUVECs grown with danazol exhibited fewer organized structures with thin and less defined interconnections than controls (see FIG. 2, in which A=control, B=1 µM danazol, C=10 µM danazol, D=50 µM danazol, and E=50 µM LY294002). Treatment with 50 µM danazol led to isolated colonies of HUVEC located in the plug with very few, thin connections or vessel lumen spaces. The effect of danazol was very similar to the positive control compound LY294002. To ensure that the vehicle used had no effect, wells were treated with ethanol at concentrations corresponding to the highest dose of danazol used and no effect on tube formation was observed (data not shown). These data indicate that danazol is an effective inhibitor of tube formation at 50 µM. Danazol had no effect on tube formation at 1 µM or 10 µM.

C. HUVEC Invasion
Protocol:

BioCoat Matrigel Invasion Chambers were purchased from BD Biosciences (San Jose, Calif.). Inserts were rehydrated at 37° C. with 500 µl HBSS for 2 hours prior to use in humidified incubator. Trypsinized HUVECs were washed twice with warm EGM-2 containing 0.1% FCS and added to the upper chamber of the invasion insert at 100,000 cells in a total volume of 250 µl. Danazol and control compounds were added to the upper reservoir at final concentrations of 10 µM and 100 µM. 750 µl EGM-2 supplemented with 5% FCS was added to the bottom chamber to initiate invasion and the plates were incubated for 24 hours. Non-invasive cells were removed from the upper chamber with moistened cotton swabs and then the inserts were washed twice with HBSS. The inserts were then submerged in 10 µM calcein AM prepared in HBSS and incubated for 4 hours. Fluorescence was determined in a microplate reader at 485 nm excitation and 595 nm emission. LY294002 and the structurally similar but inactive compound LY303511 served as positive and negative controls respectively for this experiment.

Figure 3:
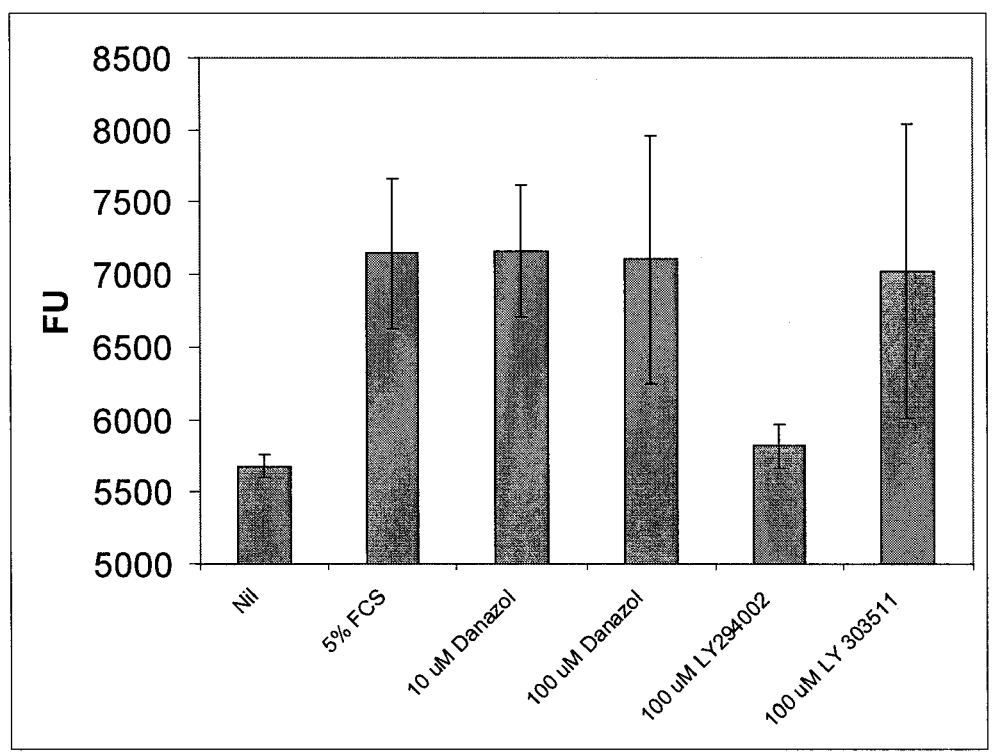
FIG. 3 shows the fluorescence measured after treatment of HUVEC cells with danazol as a measure of their ability to prevent endothelial cell invasion.

Results:

The results are presented in FIG. 3. All data is presented as representative experiment done in triplicate. Differences between subsets were analyzed using student t-test in Microsoft Excel. P<0.05 was considered statistically significant.

Porous, matrigel coated inserts were used to determine if danazol can interfere with the invasion or migration of endothelial cells (FIG. 3). In the system used for the study, a significant increase in cells was detected by fluorescent dye after the addition of FCS to the chamber opposite the endothelial cells (5674 FU±77 to 7143±516). Danazol at concentrations of 10 µM and 100 µM had no effect, while LY294002 showed almost complete attenuation of cell invasion (5814±153). These data indicate that factors present in the FCS induce the production by HUVECs of proteases that digest extracellular matrix, followed by migration along a chemotactic gradient. Danazol has no apparent inhibitory effect on invasion and migration of HUVECs in this model.

D. HUVEC Migration

Protocol:

Assays were performed to determine the effect of danazol on the migration of HUVECs in a scratch migration assay. Passage 8 HUVECs, lot number 8750 (obtained from Lonza), were plated in 6-well plates (ICS BioExpress) in endothelial growth medium-2 (EGM-2) complete medium (obtained from Lonza). The plates were cultured in a 37° C. incubator with 5% $CO_2$ for 48-72 hours to achieve confluent monolayers. The monolayers were then "scratched" with a 1000 µl pipet tip and washed two times with warm EGM-2 medium. The final wash medium was aspirated and replaced with fresh EGM-2 medium or fresh EGM-2 medium containing a range of concentrations of danazol concentrations (Sigma, #D8399). Photographs of the damaged monolayers were taken and the plates were incubated in a 37° C. incubator with 5% $CO_2$ for another 24 hours. The wells were photographed again. The gaps were measured in each photograph using Adobe Photoshop software, and gap measurements are presented as the number of pixels in the gap.

Results:

The results of three separate experiments are presented in Table 1 below. As can be seen from Table 1, danazol, at 50 µM, 75 µM and 100 µM, was found to significantly inhibit HUVEC migration in this assay. The EGM-2 culture medium used in this assay contains a cocktail of growth factors as compared to the FCS used in the Matrigel model described in section C above. This difference in the growth factors may account for the difference in the results obtained using the two models.

TABLE 1

| Compound(s) | Danazol Concentration | Mean pixels | Mean % Inhibition | STD | SEM |
|---|---|---|---|---|---|
| Diluent control (ethanol) | | 1264.00 | | | |
| Danazol | 10 µM | 1004.00 | 21.14 | 14.87 | 8.59 |
| Danazol | 25 µM | 1184.00 | 5.50 | 8.80 | 5.08 |
| Danazol | 50 µM | 895.33 | 27.64 | 17.63 | 10.18 |
| Danazol | 75 µM | 317.33 | 74.62 | 6.80 | 3.93 |
| Danazol | 100 µM | 178.67 | 85.90 | 0.92 | 0.53 |

Example 2

Danazol Effect on Vascular Permeability of HUVEC Monolayers

Protocol:

Assays were performed to determine the effect of danazol on permeability of HUVEC monolayers. Passage 5-10 HUVECs, lot number 7016 (obtained from Lonza), were seeded onto 1-micron-pore-size inserts located in the wells of a 24-well plate (Greiner BioOne 24-well Thincert cell culture inserts, #662610, or ISC BioExpress, #T-3300-15) using endothelial growth medium-2 (EGM-2) (obtained from Lonza). The plates were cultured in a 37° C. incubator with 5% $CO_2$ for 48-72 hours to achieve confluence and develop tight monolayers. The medium was then removed and replaced with fresh medium or fresh medium containing a range of danazol concentrations (Sigma, #D8399). Tumor necrosis factor α (TNFα; Pierce Biotechnology, #RTNFAI) and interleukin-1β (IL-1β; Sigma, #I-9401) were added to appropriate wells at final concentrations of 10 ng/ml each. TNFα and IL-1β induce permeability; they can cause up to a ten-fold increase in permeability. Finally, streptavidin conjugated to horseradish peroxidase (HRP) (Pierce Biotechnology, #N100, 1.25 mg/ml) was added to each well at a final dilution of 1:250. HRP is a large molecule having a molecular weight of about 44,000. Final volumes were 300 µl in the upper chambers and 700 µl in the bottom chambers of each well. The plates were incubated for an additional 24 hours in the 37° C. incubator with 5% $CO_2$. After this incubation, the inserts were removed and discarded. Visual examination of the cells on the inserts indicated that all of the monolayers were still intact.

To evaluate HRP flow-through, 15 µl of the resulting solutions in the bottom chambers were transferred to 96-well ELISA plates (each reaction performed in triplicate). Next, 100 µl of tetramethylbenzidine (TMB) solution (Pierce) were added to each well, and the color developed for 5 minutes at room temperature. Color development was stopped by adding 100 µl of 0.18 N acidic solution. OD was determined for each well using a microplate reader set at 450 nm minus 530 nm. The percent inhibition of permeability was calculated versus controls, and the means for three separate experiments are presented in Table 2.

As can be seen from Table 2, danazol at concentrations of 25.0 µM or higher actually increased vascular permeability. A concentration of 10.0 µM had little or no effect on vascular permeability. Danazol at concentrations from 0.1 µM to 5.0 µM, with 0.1 µM to 0.5 µM being optimal, decreased vascular permeability. The dose-response curve is very interesting as there is a second peak of inhibition at concentrations from 0.001 µM (or perhaps even lower) to 0.005 µM. Thus, danazol exhibits a very surprising and unexpected dose response curve for vascular permeability.

As shown in Example 1, a concentration of 50 µM to 100 µM would be required to obtain inhibition of HUVEC proliferation, migration and tube formation after 18-24 hours of incubation with danazol. As shown in this Example 2, these optimal concentrations for inhibiting angiogenesis would dramatically increase vascular permeability after 24 hours (see Table 2). Conversely, optimal concentrations for use to inhibit vascular permeability (0.1 µM to 0.5 µM) have insignificant effects on angiogenesis at 24 hours.

TABLE 2

| Compound(s) | Danazol Concentration | Mean % Inhibition | STD | SEM |
|---|---|---|---|---|
| Danazol | 0.001 µM | 19.35 | 5.39 | 3.11 |
| Danazol | 0.005 µM | 16.37 | 8.04 | 4.64 |
| Danazol | 0.01 µM | -2.74 | 14.56 | 8.40 |
| Danazol | 0.05 µM | 7.67 | 8.83 | 5.10 |
| Danazol | 0.1 µM | 35.59 | 23.08 | 11.54 |
| Danazol | 0.5 µM | 30.95 | 12.01 | 6.01 |
| Danazol | 1.0 µM | 21.20 | 31.13 | 13.92 |
| Danazol | 5.0 µM | 14.63 | 15.30 | 7.65 |
| Danazol | 10.0 µM | 14.29 | 36.85 | 13.03 |
| Danazol | 25.0 µM | -1.06 | 22.60 | 11.30 |
| Danazol | 50.0 µM | -377.36 | 384.50 | 171.95 |
| TNFα + IL-1β + Danazol | 0.1 µM | 31.30 | 25.26 | 12.63 |
| TNFα + IL-1β + Danazol | 1.0 µM | 29.22 | 16.17 | 7.23 |
| TNFα + IL-1β + Danazol | 10.0 µM | 8.47 | 20.45 | 9.14 |
| TNFα + IL-1β + Danazol | 25.0 µM | -39.93 | 15.53 | 7.76 |
| TNFα + IL-1β + Danazol | 50.0 µM | -117.16 | 29.20 | 14.60 |

Example 3

Danazol Effect on Vascular Permeability

Passage 9 human retinal endothelial cells (ACBRI 181, Applied Cell Biology Research Institute, Kirkland, Wash.) were passaged in EGM-2 medium (Lonza, Walkersville, Md.) until 80% confluence was obtained. The cells were then released from the passage flask using Trypsin-EDTA, and the cells in the resulting suspension were counted to determine both viability and cell numbers. Viability of the cell suspension was greater than 90% in this experiment.

The cells were then seeded onto inserts (1 micron pore size) located in the wells of a 24-well plate (Greiner BioOne 24-well Thincert cell culture inserts, #662610) in 300 µl EGM-2 complete medium (obtained from Lonza). Then, 700 µl EGM-2 was placed in the bottom chamber, and the plates were cultured in a 37° C. incubator with 5% $CO_2$ for 48 hours to achieve confluent monolayers. Transendothelial electrical resistance (TER) measurements were taken using an STX 100 electrode attached to $EVOM^2$ voltohmmeter (both from World Precision Instruments) for all inserts to confirm establishment of a semi-permeable barrier. To perform the measurements, one probe was placed in each well with one electrode in the upper chamber and one in the lower chamber.

Then, the cells were treated in duplicate as follows. EGM-2 medium was carefully decanted from the inserts and replaced with IMDM medium containing 0.5% fetal bovine serum and EGM-2 supplements, except for VEGF and hydrocortisone (all from Lonza). In some wells, the IMDM medium contained danazol (Sigma, #D8399) in a ten-fold serial dilution. The plates were incubated in a 37° C. incubator at 5% $CO_2$ for four hours before 30 µl of a solution containing 4% fluorescent-labelled human serum albumin was added to the upper chamber of each well. The plates were incubated in a 37° C. incubator with 5% $CO_2$ for an additional 18 hours.

After this incubation, the inserts were removed and discarded, and 200 µl of the medium from the bottom chamber was transferred to 96-well black fluoro-plates (Falcon) in triplicate. The fluorescence of each well was then measured at an excitation wavelength of 340 nm and an emission wavelength of 470 nm. Mean fluorescence units (FU) for each insert were then calculated, and duplicate readings were averaged. The results are presented in Table 3.

TABLE 3

| Danazol Concentration | Mean FU | STD |
|---|---|---|
| None | 767.13 | 8.38 |
| 0.01 µM | 688.50 | 14.94 |
| 0.1 µM | 743.90 | 8.95 |
| 1.0 µM | 783.39 | 14.59 |
| 10.0 µM | 768.99 | 18.85 |

As can be seen, the lowest concentration of danazol (0.01 µM) gave the greatest inhibition (about 10%). Control wells run with no cells gave over 4000 FU in the lower chamber, showing that the retinal endothelial monolayers were selectively permeable.

Example 4

Effect of Danazol on TER of Three Different Endothelial Cell Monolayers

Assays were performed to determine the effect of danazol on transendothelial electrical resistance (TER) of human retinal endothelial cells (ACBRI 181, Applied Cell Biology Research Institute, Kirkland, Wash.). To do so, 150,000 passage 14 human retinal endothelial cells were seeded onto inserts (1 micron pore size) located in the wells of a 24-well plate (Greiner BioOne 24-well Thincert cell culture inserts, #662610) in 300 µl EGM-2 complete medium (obtained from Lonza). Then, the plates were cultured in a 37° C. incubator with 5% $CO_2$ for 24 hours. After the incubation, the culture medium was carefully decanted and replaced with either fresh EGM-2 or fresh EGM-2 containing danazol at a final concentration of 1 µM. The plates were placed back in the incubator and cultured for an additional 144 hours. Assays were also performed in the same manner using passage 8 human brain endothelial cells and passage 8 human umbilical vein endothelial cells.

An initial TER measurement was taken for each insert using $EVOM^2$ voltohmmeter connected to an STX100 electrode (both from World Precision Instruments). Measurements were also taken at 24, 48, 72 and 144 hours. The results are presented in Tables 4, 5 and 6 below. All data are presented as TER measurements/$cm^2$ of insert with TER of blank inserts subtracted.

TABLE 4

Human Retinal Endothelial Cells

| Danazol Concentration | 0 Hours | 24 Hours | 48 Hours | 72 Hours | 144 Hours |
|---|---|---|---|---|---|
| None | 32.3 | 96.0 | 144.4 | 148.0 | 219.7 |
| 1.0 µM | 21.7 | 132.3 | 182.3 | 217.7 | 234.8 |

TABLE 5

Human Brain Endothelial Cells

| Danazol Concentration | 0 Hours | 24 Hours | 48 Hours | 72 Hours | 144 Hours |
|---|---|---|---|---|---|
| None | 41.4 | 115.7 | 176.3 | 154.0 | 151.5 |
| 1.0 µM | 32.3 | 139.9 | 188.4 | 149.5 | 125.8 |

TABLE 6

Human Umbilical Vein Endothelial Cells

| Danazol Concentration | 0 Hours | 24 Hours | 48 Hours | 72 Hours | 144 Hours |
|---|---|---|---|---|---|
| None | 82.3 | 217.2 | 276.3 | 226.8 | 227.3 |
| 1.0 µM | 70.2 | 246.0 | 364.1 | 270.7 | 286.4 |

As can be seen, danazol enhanced TER measurements (reduced ion permeability) in the retinal and umbilical vein endothelial cell monolayers. Danazol did not appear to have much effect on the TER of the brain endothelial cell monolayers, except at the earliest time point. TER is a measurement of the electrical resistance across cellular monolayers. It is an indication of barrier integrity and correlates with ion permeability.

Example 5

Danazol Effect on Akt Phosphorylation

Assays were performed to determine the effect of danazol on phosphorylation of Akt in human retinal endothelial cells (ACBRI 181, Applied Cell Biology Research Institute, Kirkland, Wash.). The cells were grown in a 25 cm² flask to near confluence in EGM-2 medium (Lonza, Walkersville, Md.) containing 2% fetal calf serum (Lonza). The cells were then released from the passage flask using Trypsin/EDTA. The cells in the resulting suspension were counted and seeded on a 96-well plate at $1 \times 10^4$ cells/well in EGM-2 medium. The plate was incubated at 37° C. with 5% $CO_2$ for 24 hours. Then, 200 µl of either EGM-2 medium (control) or various concentrations of danazol were added, and the plates were incubated for an additional 2 hours. After this incubation, the cells were fixed immediately with 4% formaldehyde, refrigerated, and the extent of phosphorylation of Akt determined using the Akt Cellular Activation of Signaling ELISA Kit (CASE™ Kit for AKT S473; SABiosciences, Frederick, Md.) following the manufacturer's protocols. The CASE™ Kit for AKT S473 quantifies the amount of activated (phosphorylated) Akt protein relative to total Akt protein in parallel assays using a conventional ELISA format with colorimetric detection. The Akt phosphorylation site is serine 473 and is recognized by one of the antibodies used in one of the two parallel assays to provide a measure of activated Akt protein. The other antibody used in the other parallel assay recognizes Akt to provide a measure of total Akt protein. Both primary antibodies are detected using a horseradish peroxidase-labeled secondary antibody. Addition of the manufacturer's Developing Solution for 10 minutes, followed by addition of the manufacturer's Stop Solution, produces the result which can be measured colorimetrically.

The results are presented in Table 7 below. As can be seen there, all of the concentrations of danazol caused an increase in Akt phosphorylation (activation).

TABLE 7

| TREATMENT | PERCENT INCREASE IN AKT PHOSPHORYLATION VERSUS CONTROL | STANDARD DEVIATION |
|---|---|---|
| 0.5 µM danazol | 73.8% | 92.9% |
| 1.0 µM danazol | 66.7% | 11.7% |
| 2.0 µM danazol | 101.6% | 9.1% |
| 5.0 µM danazol | 40.5% | 17.7% |
| 10.0 µM danazol | 115.3% | 112.9% |
| 20.0 µM danazol | 161.3% | 128.7% |
| 50.0 µM danazol | 98.6% | 61.2% |

It is believed that these results provide a possible explanation for the vascular permeability dose response curve obtained in Example 2. As shown in Example 2, low doses of danazol reduced permeability, while high doses increased permeability. It is believed that a certain level of phosphorylation of Akt at S473 reduces permeability (the 0.5-5.0 µM concentrations in this experiment), while hyperphosphorylation of Akt at S473 causes increased permeability (the 10-50 µM concentrations in this experiment).

Example 6

Effect of Danazol and Steroid Receptor Antagonists on TER of Retinal Endothelial Cell Monolayers Assays were performed to determine the effect of danazol and steroid receptor antagonists on transendothelial electrical resistance (TER) of human retinal endothelial cells (ACBRI 181, Applied Cell Biology Research Institute, Kirkland, Wash.). To do so, Greiner tissue culture well inserts (Greiner BioOne 24-well Thincert cell culture inserts, #662610) were coated with 5 µg/cm² fibronectin (Sigma). Then, passage 12 human retinal endothelial cells were seeded into the upper chamber of the wells at 120,000 cells per insert in a volume of 300 µl of EGM-2 medium (Lonza). The volume for the lower chamber was 700 µl of EGM-2 medium (Lonza). The plates were cultured in a 37° C. incubator with 5% $CO_2$ for 48 hours to establish intact monolayers. At the end of the incubation, TER measurements were taken using an STX 2 probe attached to EVOM² voltohmmeter (both from World Precision Instruments) for all inserts to confirm integrity of the endothelial barrier. All inserts exhibited elevated resistance as compared to inserts without cells.

Then, the culture medium was carefully decanted and replaced with fresh EGM-2, with and without several additives. The additives were danazol, hydroxyflutamide (androgen receptor antagonist), fluvestrant (estrogen antagonist) and PI3 kinase inhibitor LY 294002 (control). Stock solutions of all additives, except danazol, were made at 10 mM in DMSO. The danazol stock solution was 10 mM in ethanol. Working 200 µM dilutions of all additives were made in same solvents. Then, 200 nM dilutions of each additive, and of equivalent dilutions of ethanol and DMSO (controls), were made in EGM-2 medium, and danazol and each of the other additives or medium (control) were added to the wells in the combinations and final concentrations shown in the table below. The plates were then placed back into the incubator, and TER measurements were taken as described above for each insert at 30 minutes, 60 minutes, 120 minutes and 24 hours. TER was calculated by subtracting the background measurement (empty insert) from the reading of an insert and dividing by the surface area of the insert (0.33 cm²). The results are presented in Table 8 below.

TABLE 8

| Treatment | TER at 30 minutes | TER at 60 minutes | TER at 120 minutes | TER at 24 Hours |
|---|---|---|---|---|
| None | 216.22 | 249.25 | 234.23 | 312.31 |
| 0.1 µM Danazol | 255.26 | 267.27 | 249.35 | 366.37 |
| 0.1 µM Hydroxyflutamide | 177.18 | 186.19 | 201.20 | 297.30 |
| 0.1 µM Fluvestrant | 228.23 | 270.27 | 258.26 | 336.34 |
| 0.1 µM Hydroxyflutamide followed by 0.1 µM Danazol | 237.24 | 276.28 | 240.24 | 363.36 |
| 0.1 µM Fluvestrant followed by 0.1 µM Danazol | 195.20 | 309.31 | 255.26 | 393.39 |
| 10.0 µM LY294002 | 297.30 | 354.35 | 276.28 | 345.35 |
| 10.0 µM LY294002 followed by 0.1 µM Danazol | 243.24 | 342.34 | 270.27 | 336.34 |

As can be seen from Table 8, danazol and fluvestrant increased the TER measurements (reduced permeability), while hydroxyflutamide reduced the readings (increased permeability), compared to the control (no treatment). Danazol prevented the reduction caused by hydroxyflutamide. This could be evidence that danazol is occupying the androgen receptor in these cells. Danazol and fluvestrant showed additive results at some time points.

Example 7

Effect of Danazol on Actin Stress Fiber Formation

The IEJs of the paracellular pathway include AJs and TJs. The actin cytoskeleton is bound to each junction and control the integrity of the junctions through actin remodeling. Reorganization of the actin filaments into stress fibers results in application of mechanical forces to the junctions that pull them apart, cause cellular contraction and changes in morphology. The process of actin polymerization is very dynamic, which allows for the rapid reorganization of actin structures and the transition from the quiescent phenotype, characterized by thick cortical actin ring and the absence of stress fibers, to the activated cell phenotype with thin or no cortical actin and abundant stress fibers. The actin cytoskeleton appears also to be involved in transcytosis, perhaps by regulating the movement of caveolae.

Human retinal endothelial cells (ACBRI 181, Applied Cell Biology Research Institute, Kirkland, Wash.) were seeded into Falcon Optilux assay plates (BD Biosciences) at 1000 cells per well in a total volume of 200 µl of EGM-2 medium (Lonza). The plates were cultured in a 37° C. incubator with 5% $CO_2$ for 48 hours. Then, the medium was removed and replaced with 200 µl of IMDM medium supplemented with 0.1% fetal bovine serum (all from Lonza), and the cells were cultured under these growth factor and serum starved conditions for one hour to suppress actin polymerization. Then danazol (0.1 µM or 10 µM final concentrations) or the PI3 kinase inhibitor LY294002 (10 µM final concentration) (positive control) were added. Immediately following addition of these compounds, TNFα (final concentration of 50 ng/ml) was added. After incubation for 30 minutes in a 37° C. incubator with 5% $CO_2$, the medium was aspirated, and the cells were fixed with 3.6% formaldehyde in phosphate buffered saline (PBS) for ten minutes at room temperature. All wells were then washed two times with 100 µl PBS. The cells were permeabilized using a 0.1% Triton X-100 in PBS for 5 minutes. All wells were then washed two times with 100 µl PBS, and 50 µl of a 1:40 dilution of rhodamine-phalloidin (Invitrogen) in PBS was added to the cells to stain for F-actin and left on the cells for 20 minutes at room temperature. All wells were then washed two times with 100 µl PBS. Then 100 µl PBS was added to each well and the cells were observed and photographed using an inverted microscope with rhodamine filters (ex530/em590).

The results showed that danazol affected the ability of stress fibers to develop. When treated with danazol, the cells exhibited different staining patterns, dependent on the dosage. At the lower danazol dose (0.1 µM), diffuse staining throughout the cytoplasm was observed, possibly indicative of a stabilizing event or of a resting phenotype. At the higher danazol dose (10.0 µM), stress fibers with multiple focal points were detected. These findings correlate with previous results (see previous examples) that lower danazol doses inhibit permeability and higher danazol doses increase permeability. TNFα stimulated the cells and led to strong stress fiber development with intensely staining focal points. Danazol and LY294002 decreased the number of cells exhibiting stress fiber development with TNFα.

Example 8

Effect of Danazol on Actin Stress Fiber Formation

Human retinal endothelial cells (ACBRI 181, Applied Cell Biology Research Institute, Kirkland, Wash.) were seeded into Falcon Optilux assay plates (BD Biosciences) coated with 1 µg/cm² fibronectin at 3000 cells per well in a total volume of 200 µl of EGM-2 medium (Lonza). The plates were cultured in a 37° C. incubator with 5% $CO_2$ for 48 hours. Then, the medium was removed and replaced with 200 µl of Ultraculture medium supplemented with 2.0% fetal bovine serum (all from Lonza), and the cells were cultured under these growth factor and serum starved conditions overnight to suppress actin polymerization. Then, the medium was removed and replaced with fresh Ultraculture medium supplemented with 2.0% fetal bovine serum containing danazol (0.1 µM, 1 µM or 10 µM) or the PI3 kinase inhibitor LY294002 (10 µM) (positive control). After incubation with these compounds for 30 minutes in a 37° C. incubator with 5% $CO_2$, vascular endothelial growth factor (VEGF) (final concentration of 25 ng/ml) was added. After incubation for an additional 30 minutes in a 37° C. incubator with 5% $CO_2$, the medium was aspirated, and the cells were fixed using 3.6% formaldehyde in phosphate buffered saline (PBS) for ten minutes at room temperature. All wells were then washed two times with 100 µl PBS. The cells were permeabilized using a 0.1% Triton X-100 in PBS for 5 minutes. All wells were then washed two times with 100 µl PBS, and 50 µl of a 1:40 dilution of rhodamine-phalloidin (Invitrogen) in PBS was added to the cells to stain for F-actin and left on the cells for 20 minutes at room temperature. All wells were then washed two times with 100 µl PBS. To counter-stain for nuclei, 100 µl of a 3 µM DAPI (4,6-diamidino-2-phenylindole, dilactate (Invitrogen)) solution was added to each well. After 5 minutes, the cells were washed two times with 100 µl PBS. Then 100 µl PBS was added to each well and the cells were observed and photographed using an inverted microscope using rhodamine (ex530/em590) and DAPI (ex350/em460) filters.

The results showed that danazol affected the ability of stress fibers to develop. When treated with danazol, the cells exhibited different stress fiber formation patterns, dependent on the dosage applied. At the lowest danazol dose (0.1 µM), diffuse F-actin staining throughout the cytoplasm was observed. At 1.0 µM danazol, the diffuse staining persisted, but stress fibers and focal points around the perimeter of most cells were visible. At the highest danazol dose (10.0 µM), there was no longer any diffuse staining, and stress fiber development and focal points were seen. The staining seen with the lower doses of danazol exhibited a perinuclear staining pattern, indicating microtubule stabilization similar to that observed with paclitaxel (a Taxol compound known to stabilize and polymerize microtubules). With VEGF, there was strong stress fiber development. Danazol changed the VEGF pattern in a dose-dependent manner: (i) the lowest 0.1 µM danazol dose made the stress fibers less pronounced and some diffuse staining appeared; (ii) the 1.0 µM dose showed fewer thick stress fibers, but focal points were seen on contact surfaces; and (iii) the highest 10.0 µM danazol dose showed strong stress fiber development with focal points. LY294002 prevented the strong stress fiber development seen with VEGF and exhibited diffuse staining.

Example 9

Effect of Danazol on Vascular Endothelial Cadherin (VE-Cadherin) Phosphorylation Passage 12 human retinal endothelial cells (ACBRI 181, Applied Cell Biology Research Institute, Kirkland, Wash.) were grown to confluence on fibronectin-coated (1 µg/cm²) 10 cm² tissue culture plates using EGM-2 culture medium (Lonza) in a 37° C. incubator with 5% $CO_2$. When complete confluence was achieved, the medium was replaced with Ultraculture medium supplemented with 0.5% fetal bovine serum and L-glutamine (all from Lonza), and the cells were cultured under these growth factor and serum starved conditions for 24 hours. Then, the medium was removed and replaced with fresh Ultraculture medium supplemented with 0.5% fetal bovine serum and L-glutamine containing danazol (0.1 µM, 1 µM or 10 µM) or ethanol (vehicle control). After incubation for 15 minutes in a 37° C. incubator with 5% $CO_2$, vascular endothelial growth factor (VEGF) (final concentration of 50 ng/ml) was added, and the plates incubated for an additional 15 minutes in a 37° C. incubator with 5% $CO_2$ The plates were immediately treated to lyse the cells as follows. PBS and the lysis buffer (PBS containing 1% Triton X-100 supplemented with phosphatase inhibitor solutions 1 and 2 (Sigma), protease inhibitor (Sigma) and sodium orthovanadate at a final concentration of 2 mM) were cooled to 4° C. The cells were washed two times with 5 ml of the ice cold PBS and then lysed in 500 µl of the ice cold lysis buffer. The resulting protein extracts were transferred to 1.7 ml microcentrifuge tubes, and cell debris was removed by spinning at 4° C. at 10,000 rpm for 10 minutes. Then, 450 µl of the cleared solution was transferred to tubes containing 25 µl of Protein Dynabeads (Invitrogen) coated with 10 µl C19 anti-VE cadherin polyclonal antibody (Santa Cruz Biotechnology) (coating performed following manufacturer's protocol). The extracts and beads were then incubated overnight at 4° C. on an orbital shaker to capture VE cadherin from the extracts. The beads were then washed four times with ice cold lysis buffer. To release the protein from the beads, they were heated for 10 minutes at 75° C. in SDS loading dye containing 20% reducing dye (Invitrogen).

The released proteins were separated in 4-20% polyacrylamide gels (Invitrogen) at 120 volts for 1 hour. To determine phosphorylation and total protein in the gels, Pro-Q diamond (Invitrogen) and SYPRO ruby (Invitrogen) protein staining were sequentially performed following the manufacturer's protocol. The gels were photographed and densitometry performed using a Kodak imaging station. The results are presented in Table 9 below.

TABLE 9

VE-Cadherin

|  | Nil (ethanol control) | 0.1 µM danazol | VEGF | 0.1 µM danazol followed by VEGF |
|---|---|---|---|---|
| Relative intensity - ProQ results (phosphorylated protein) | 1.00 | 1.51 | 1.89 | 1.38 |
| Relative intensity - SYPRO results (total protein) | 1.00 | 0.89 | 0.84 | 0.83 |
| Ratio phosphorylated:total protein | 0.215 | 0.365 (1.70 fold increase) | 0.481 (2.24 fold increase) | 0.358 (1.66 fold increase) |

As can be seen, danazol caused an increase in VE-cadherin phosphorylation. VEGF caused an even greater increase in VE-cadherin phosphorylation (hyperphosphorylation), which was reversed by danazol. VE-cadherin is a component of AJs, and phosphorylation of VE-cadherin can have a variety of effects depending on the residue. In general, tyrosine phosphorylation of VE-cadherin leads to AJ disassembly and increased permeability. Serine 665 phosphorylation, however, causes a rapid but reversible internalization of VE-cadherin associated with reduced barrier function. A feedback loop appears to exist in which internalized VE-cadherin drives an increase in cytoplasmic p120, a scaffolding protein that complexes to AJs. This up-regulation induces a decrease in active RhoA in association with an increase in the barrier-stabilizing GTPases like Rac1, Rap-1, and Cdc42. It is believed that the increase in VE-cadherin phosphorylation observed in this experiment following low dose danazol treatment leads to the activation of barrier stabilizing GTPases. In addition, danazol may prevent the destabilizing phosphorylation events induced by VEGF.

Example 10

Effect of Danazol and Steroid Receptor Antagonists on TER of Retinal Endothelial Cell Monolayers Assays were performed to determine the effect of danazol and steroid receptor antagonists on transendothelial electrical resistance (TER) of human retinal endothelial cells (ACBRI 181, Applied Cell Biology Research Institute, Kirkland, Wash.). To do so, Greiner tissue culture well inserts (Greiner BioOne 24-well Thincert cell culture inserts, #662610) were coated with 5 µg/cm² fibronectin. Then, passage 13 human retinal endothelial cells were seeded into the upper chamber of the wells at 120,000 cells per insert in a volume of 300 µl of EGM-2 medium (Lonza). The volume for the lower chamber was 700 µl of EGM-2 medium (Lonza). The plates were cultured in a 37° C. incubator with 5% $CO_2$ for 48 hours to establish intact monolayers. At the end of the incubation, TER measurements were taken using an STX 2 probe attached to $EVOM^2$ voltohmmeter (both from World Precision Instruments) for all inserts to confirm integrity of the endothelial barrier. All inserts exhibited elevated resistance as compared to inserts without cells.

Then, the culture medium was carefully decanted and replaced with fresh EGM-2, with and without several additives. The additives were danazol, hydroxyflutamide (androgen receptor antagonist), fluvestrant (estrogen antagonist), testosterone, estradiol and PI3 kinase inhibitor LY 294002 (control). Stock solutions of all additives, except danazol, were made at 10 mM in DMSO. The danazol stock solution was 10 mM in ethanol. Working 200 µM dilutions of all additives were made in same solvents. Then, 200 nM dilutions of each additive, and of equivalent dilutions of ethanol and DMSO (controls), were made in EGM-2 medium, and danazol and each of the other additives or medium (control) were added to the wells in the combinations and final concentrations shown in the table below. The plates were then placed back into the incubator, and TER measurements were taken as described above for each insert at 5 minutes, 30 minutes, 60 minutes and 24 hours. TER was calculated by subtracting the background measurement (empty insert) from the reading of an insert and dividing by the surface area of the insert (0.33 cm²). The results are presented in Table 10 below.

As can be seen from Table 10, danazol increased the TER measurements, hydroxyflutamide reduced the readings, testosterone reduced the readings very slightly, and fluvestrant had essentially no effect, compared to the control (no treatment). Danazol prevented the reduction caused by hydroxyflutamide and the very slight reduction seen with testosterone. As with the results in Example 6, this could be evidence that danazol is occupying the androgen receptor in these cells.

TABLE 10

| Treatment | TER at 5 minutes | TER at 30 minutes | TER at 60 minutes | TER at 24 Hours |
|---|---|---|---|---|
| None | 250.30 | 262.31 | 251.00 | 287.09 |
| 0.1 µM Danazol | 280.03 | 311.56 | 313.06 | 348.35 |
| 0.1 µM Hydroxyflutamide | 190.44 | 207.46 | 215.97 | 267.27 |
| 0.1 µM Hydroxyflutamide followed by 0.1 µM Danazol | 230.48 | 275.53 | 262.01 | 312.31 |
| 0.1 µM Fluvestrant | 223.47 | 251.50 | 243.99 | 279.28 |
| 0.1 µM Fluvestrant followed by 0.1 µM Danazol | 219.47 | 279.53 | 273.02 | 343.34 |

TABLE 10-continued

| Treatment | TER at 5 minutes | TER at 30 minutes | TER at 60 minutes | TER at 24 Hours |
|---|---|---|---|---|
| 10 nM Testosterone | 257.51 | 240.49 | 225.98 | 267.27 |
| 100 nM Testosterone followed by 0.1 µM Danazol | 273.52 | 287.54 | 259.01 | 283.28 |
| 10 nM Estradiol | 246.50 | 245.50 | 250.00 | 328.33 |
| 10 nM Estradiol followed by 0.1 µM Danazol | 276.53 | 307.56 | 282.03 | 363.36 |

Example 11

Effect of Danazol on Actin Stress Fiber Formation

Passage 6 human renal glomerular microvascular endothelial cells (ACBRI 128, Cell Systems Corporation (exclusive distributor for Applied Cell Biology Research Institute), Kirkland, Wash.) and passage 12 human retinal endothelial cells (ACBRI 181, Cell Systems Corporation (exclusive distributor for Applied Cell Biology Research Institute), Kirkland, Wash.) were seeded into 16-chamber glass slides coated with 5 µg/cm² fibronectin at 2000 cells per well in a total volume of 200 µl of EGM-2 medium (Lonza). The plates were cultured in a 37° C. incubator with 5% $CO_2$ for 48 hours with daily medium changes. Then, the test compounds (danazol, TNFα and S1P), diluted in Hanks Balanced Salt Solution (HBSS; Lonza), were added to give the following final concentrations: danazol (1 µM) (Sigma), TNFα (1 ng/ml) (Sigma), and SIP (1 µM) (Sigma). The slides were incubated with the test compounds for 15 minutes, 30 minutes or 24 hours in a 37° C. incubator with 5% $CO_2$. After this incubation, the medium was aspirated, and the cells were fixed using 3.6% formaldehyde in phosphate buffered saline (PBS) for ten minutes at room temperature. All wells were then washed two times with 100 µl PBS. The cells were permeabilized using a 0.1% Triton X-100 in PBS for 5 minutes. All wells were then washed two times with 100 µl PBS, and 50 µl of a 1:40 dilution of rhodamine-phalloidin (Invitrogen) in PBS was added to the cells to stain for F-actin and left on the cells for 20 minutes at room temperature. All wells were then washed two times with 100 µl PBS. Then 100 µl PBS was added to each well and the cells were observed and photographed using an inverted microscope using a rhodamine (ex530/em590) filter.

The results showed that danazol affected the ability of stress fibers to develop in the renal glomerular microvascular endothelial cells. When treated with danazol alone, the cells exhibited perinuclear staining at 15 minutes, diffuse staining throughout the cells with ruffled edges on many of the cells at 3 hours, and staining similar to untreated controls at 24 hours. With TNFα alone, stress fibers were seen at all times, with the number of cells exhibiting stress fibers and the thickness of the fibers increasing with time. Danazol decreased the stress fiber formation and the thickness of the fibers at all times, and cortical actin rings and ruffled edges were visible beginning at 3 hours. Cells treated with S1P alone showed actin cortical rings, with development beginning at 15 minutes and strongest at 3 hours. The cells were returning to morphology similar to untreated controls at 24 hours. Danazol seemed to enhance the cortical rings. Also, diffuse staining was observed, especially at 15 minutes and 24 hours.

For the retinal endothelial cells treated with danazol alone, the cells exhibited perinuclear staining at 15 minutes, diffuse staining throughout the cells with ruffled edges on many of the cells at 3 hours, and staining similar to untreated controls at 24 hours. With TNFα alone, stress fibers were seen at all times, with the number of cells exhibiting stress fibers and the thickness of the fibers increasing from 15 minutes to 3 hours and being reduced after 24 hours of incubation. Danazol decreased the stress fiber formation and/or the thickness of the fibers at all times. Diffuse staining was observed at 15 minutes and 24 hours, and cortical actin rings were visible at 3 hours. Cells treated with S1P alone showed actin cortical rings, with development beginning at 15 minutes and strongest at 3 hours. The cells were returning to morphology similar to untreated controls at 24 hours. Danazol seemed to enhance the cortical rings at 3 hours. Also, diffuse staining was observed, especially at 15 minutes and 24 hours.

S1P (sphingosine-1 phosphate) plays a very important function in the formation and maintenance of vascular endothelium. S1P is a constitutive signaling input that facilitates the organization and barrier function of the vascular endothelium through its effects on the actin cytoskeleton. In particular, S1P is involved in the formation of cortical actin fibers and organization of the adherens junctions. Depletion of S1P leads to vascular leak and edema, and S1P can reverse endothelial dysfunction and restore barrier function.

In this experiment, danazol exhibited an ability to strengthen the protective effects of S1P in both retinal and glomerular endothelial cells. Danazol also reversed the formation of stress fibers induced by TNFα in both of these types of endothelial cells. Diffuse perinuclear staining is seen in cells treated with danazol alone.

Example 12

Effect of Danazol on ECIS

Assays were performed to determine the effect of danazol on transendothelial electrical resistance (TER) of human renal glomerular microvascular endothelial cells (ACBRI 128, Cell Systems Corporation (exclusive distributor for Applied Cell Biology Research Institute), Kirkland, Wash.) or human retinal endothelial cells (ACBRI 181, Cell Systems Corporation (exclusive distributor for Applied Cell Biology Research Institute), Kirkland, Wash.). Electrical resistance was measured using the electric cell-substrate impedance sensing (ECIS) system (ECISZθ, obtained from Applied Biophysics) with 8-well multiple electrode plates (8W10E). Each well of the plates was coated with 5 µg/cm² fibronectin in HBSS by adding the fibronectin in a volume of 100 µl per well and incubating the plates for 30 minutes in a 37° C. incubator with 5% $CO_2$. The fibronectin solution was removed, and 400 µl of EGM-2 culture medium (Lonza) was added to each well. The plates were connected to the ECISZθ system and were electrically stabilized. The EGM-2 medium was aspirated and replaced with 200 µl of EGM-2 culture medium containing 100,000 cells per well. The plates were reconnected to the ECISZθ system and incubated for 24 hours in a 37° C. incubator with 5% $CO_2$. The EGM-2 medium was aspirated and replaced with 400 µl of fresh EGM-2 culture medium per well. The plates were reconnected to the ECISZθ system and incubated for 6 hours in a 37° C. incubator with 5% $CO_2$. Concentrated solutions of the test compounds in HBSS were prepared and placed in the incubator to equilibrate. The test compounds were then added to appropriate wells at the following final concentrations: danazol (1 μM) (Sigma) and S1P (1 μM) (Sigma). ECIS (resistance) was monitored for 90 hours.

In the retinal endothelial cells, 1.0 μM danazol alone showed an increase of ECIS as compared to untreated cells starting about 1.5-2.0 hours after treatment and persisting for 5 hours. S1P alone showed an increase of ECIS as compared to untreated cells which started within the first 15 minutes after treatment and persisted for about 3 hours. Danazol and S1P in combination increased the ECIS as compared to S1P alone and untreated cells, and this increased ECIS persisted for about 90 hours. Thus, danazol exhibited an ability to enhance the early effects of S1P and to maintain a higher resistance throughout the experiment when S1P was present.

Glomerular endothelial cells exhibited a different pattern. Danazol alone had no effect on ECIS until about 30 hours after treatment. Danazol alone increased ECIS compared to untreated cells from about 30 to about 90 hours, with the greatest increase occurring between about 60-90 hours. S1P alone also had no effect on ECIS until about 30 hours after treatment. S1P alone increased ECIS compared to untreated cells from about 30 to about 60 hours. The combination of danazol and S1P had no effect on ECIS until about 30 hours after treatment. This combination increased ECIS compared to untreated cells, S1P alone and danazol alone. In particular, the combination increased ECIS compared to untreated cells from about 30 to about 70 hours, increased ECIS compared to S1P alone from about 30 to 75 hours, and increased ECIS compared to danazol alone from about 30 to about 50 hours.

Example 13

Effect of Danazol on ECIS

Assays were performed to determine the effect of danazol on transendothelial electrical resistance (TER) of human renal glomerular microvascular endothelial cells (ACBRI 128, Cell Systems Corporation (exclusive distributor for Applied Cell Biology Research Institute), Kirkland, Wash.). Electrical resistance was measured using the electric cell-substrate impedance sensing (ECIS) system (ECISZθ, obtained from Applied Biophysics) with 8-well multiple electrode plates (8W10E). Each well of the plates was coated with 5 μg/cm$^2$ fibronectin in HBSS by adding the fibronectin in a volume of 50 μl per well and incubating the plates for 30 minutes in a 37° C. incubator with 5% $CO_2$. The fibronectin solution was removed, and 200 μl of EGM-2 culture medium (Lonza) was added to each well. The plates were connected to the ECISZθ system and were electrically stabilized. The EGM-2 medium was aspirated and replaced with 200 μl of EGM-2 culture medium containing 40,000 passage 6 cells per well. The plates were reconnected to the ECISZθ system and incubated for 24 hours in a 37° C. incubator with 5% $CO_2$. The EGM-2 medium was aspirated and replaced with 200 μl of fresh EGM-2 culture medium per well. The plates were reconnected to the ECISZθ system and incubated for an additional 24 hours in a 37° C. incubator with 5% $CO_2$. The EGM-2 medium was aspirated and replaced with 200 μl of fresh EGM-2 culture medium without dexamethasone per well. The plates were reconnected to the ECISZθ system and incubated overnight in a 37° C. incubator with 5% $CO_2$. Finally, the EGM-2 medium was aspirated and replaced with 200 μl of fresh EGM-2 culture medium without dexamethasone per well. The plates were reconnected to the ECISZθ system and incubated 2 hours in a 37° C. incubator with 5% $CO_2$. Concentrated solutions of the test compounds in HBSS were prepared and placed in the incubator to equilibrate. The test compounds were then added to appropriate wells at the following final concentrations: danazol (1 μM) (Sigma) and dexamethasone (1 μM) (Sigma). ECIS (resistance) was monitored for 90 hours.

Danazol alone increased ECIS compared to untreated cells beginning at about 3 hours and persisting for about 90 hours. The increase was greatest from about 12 to about 15 hours. When compared to dexamethasone, danazol exhibited a similar pattern, but the enhancement of ECIS (TER) was not as great.

Example 14

Effect of Danazol on RhoA

Remodeling of the endothelial cell cytoskeleton is central to many functions of the endothelium. The Rho family of small GTP-binding proteins have been identified as key regulators of F-actin cytoskeletal dynamics. The Rho family consists of three isoforms, RhoA, RhoB and RhoC. The activation of RhoA activity leads to prominent stress fiber formation in endothelial cells. Stimulation of endothelial cells with thrombin increases Rho GTP and myosin phosphorylation, consistent with increased cell contractility. Inhibition of RhoA blocks this response and the loss of barrier function, demonstrating a critical role for Rho in vascular permeability.

This experiment was performed using a commercially-available Rho activation assay (GLISA) purchased from Cytoskeleton, Denver, Colo., following the manufacturer's protocol. Briefly, passage 8 or 12 human retinal endothelial cells (ACBRI 181, Applied Cell Biology Research Institute, Kirkland, Wash.) were cultured on fibronectin-coated (1 μg/cm$^2$) 6-well tissue culture plates using EGM-2 culture medium (Lonza) for 24 hours in a 37° C. incubator with 5% $CO_2$ (30,000 cells/well in total volume of 3 ml). Then, the medium was aspirated and replaced with Ultraculture medium supplemented with 0.1% fetal bovine serum, L-glutamine, sodium pyruvate, penicillin/streptomycin and ITSS (insulin, transferrin sodium selenium) (all from Lonza) to serum starve the cells and reduce the background level of RhoA. The cells were cultured for 24 hours in a 37° C. incubator with 5% $CO_2$. Test compounds diluted in HBSS were placed in the incubator to equilibrate before addition to the cells. Then, 150 μl of each test compound was added to the appropriate culture wells, and the plates were incubated in the incubator for an additional 15 minutes. Then, thrombin was added to appropriate wells. After 1 minute, the cells were washed one time with 1.5 ml phosphate buffered saline and were then lysed with 100 μl GLISA lysis buffer supplemented with protease inhibitors. The extracts were scraped, transferred to microcentrifuge tubes and transferred to ice to preserve the active form of RhoA. All extracts were then cleared of debris by spinning at 10,000 rpms for 2 minutes at 4° C. The supernatants were transferred to new tubes and placed back on ice. Aliquots of each extract were removed for the GLISA assay and for protein determinations. All protein concentrations were within 10%, and the extracts were used at the achieved concentrations (equates to 15 μg total protein per well). The GLISA assay was performed using the reagents supplied in the kit.

The results for the passage 12 retinal endothelial cells are presented in Table 11 below. As expected, the active Rho A levels induced by thrombin were very high. All of the test compounds inhibited the thrombin-induced activation of Rho A.

The results for the passage 8 retinal endothelial cells are presented in Table 12 below. As expected, the active Rho A levels induced by thrombin were very high. All of the test compounds inhibited the thrombin-induced activation of Rho A.

TABLE 11

| Treatment | Mean OD | Percent Inhibition vs. Untreated Control | Percent Inhibition vs. Thrombin |
|---|---|---|---|
| Untreated | 0.455 | — | — |
| 1.0 μM Danazol | 0.424 | 6.82 | — |
| 1.0 μM Dexamethasone | 0.428 | 5.83 | — |
| 10.0 μM PI3 kinase inhibitor LY 294002 | 0.370 | 18.70 | — |
| 1.0 μM Src-1 Inhibitor* | 0.349 | 23.21 | — |
| 0.1 U/ml Thrombin | 1.013 | — | — |
| 0.1 U/ml Thrombin + 1.0 μM Danazol | 0.859 | — | 27.57 |
| 0.1 U/ml Thrombin + 1.0 μM Dexamethasone | 0.826 | — | 33.48 |
| 0.1 U/ml Thrombin + 10.0 μM PI3 kinase inhibitor LY294002 | 0.685 | — | 58.73 |
| 0.1 U/ml Thrombin + 1.0 μM Src-1 Inhibitor | 0.534 | — | 85.85 |

*Obtained from Sigma.

TABLE 12

| Treatment | Mean OD | Percent Inhibition vs. Untreated Control | Percent Inhibition vs. Thrombin |
|---|---|---|---|
| Untreated | 0.102 | — | — |
| 1.0 μM Danazol | 0.027 | 73.89 | — |
| 10.0 μM PI3 kinase inhibitor LY 294002 | 0.056 | 45.32 | — |
| 0.1 U/ml Thrombin | 0.561 | — | — |
| 0.1 U/ml Thrombin + 1.0 μM Danazol | 0.373 | — | 41.02 |
| 0.1 U/ml Thrombin + 10.0 μM PI3 kinase inhibitor LY294002 | 0.433 | — | 27.86 |

Example 15

Animal Model of Vascular Hyperpermeability

New Zealand white rabbits received 0.215 mg/kg of danazol orally twice per day for 7 days. The rabbits were then injected once intravitreally with vascular endothelial growth factor A (VEGF-A) to produce vascular leakage in the retina. Then, 24 hours later, fluorescein sodium was injected, and the fluorescence of the eyes was measured using a Fluorotron (Ocumetrics) (five measurements averaged). A single control (placebo) rabbit had 250 fluorescence units in the retina, indicating vascular leakage there. A single danazol-treated rabbit gave 16 fluorescence units, which represents a 94% reduction in vascular leakage caused by the danazol.

What is claimed:

1. A method of treating macular edema in a human comprising orally administering to the human a vascular-hyperpermeability-inhibiting amount of danazol or a pharmaceutically acceptable salt thereof, wherein the hyperpermeability-inhibiting amount is from 1 mg to 100 mg per day.

2. The method of claim 1 wherein the vascular-hyperpermeability-inhibiting amount is from 10 mg to 90 mg per day.

3. The method of claim 1 wherein the macular edema is caused by a vascular occlusion, a post-intraocular surgery, a uveitis or a retinitis.

4. The method of claim 1 wherein the macular edema is diabetic macular edema.

5. The method of claim 1 wherein the human has diabetic retinopathy.

6. The method of claim 5 wherein the diabetic retinopathy is nonproliferative diabetic retinopathy.

7. The method of claim 1 wherein the vascular-hyperpermeability-inhibiting amount of the danazol or pharmaceutically acceptable salt thereof is administered to the human at the appearance of one or more early signs of, or a predisposition to develop, macular edema.

8. The method of claim 1 wherein the vascular-hyperpermeability-inhibiting amount of the danazol or pharmaceutically acceptable salt thereof is administered to the human immediately upon diagnosis of macular edema.

9. The method of claim 1 wherein the macular edema is from vascular-hyperpermeability of a continuous endothelium found in, or around, a retina.

* * * * *